United States Patent
Lee et al.

(10) Patent No.: US 9,512,193 B2
(45) Date of Patent: Dec. 6, 2016

(54) P15 PROTEIN VARIANT AND USE THEREOF FOR PREVENTING OR TREATING CANCER

(71) Applicant: Samsung Electronics Co., Ltd., Suwon-si, Gyeonggi-do (KR)

(72) Inventors: Jung-Hoon Lee, Hwaseong-si (KR); Jae Il Lee, Yongin-si (KR); Eunji Kang, Gyeonggi-do (KR); Jungmin Lee, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 115 days.

(21) Appl. No.: 14/615,224

(22) Filed: Feb. 5, 2015

(65) Prior Publication Data
US 2015/0218243 A1 Aug. 6, 2015

(30) Foreign Application Priority Data
Feb. 5, 2014 (KR) .................. 10-2014-0013239

(51) Int. Cl.
*C07K 14/47* (2006.01)
*A61K 38/00* (2006.01)

(52) U.S. Cl.
CPC ....... *C07K 14/4738* (2013.01); *C07K 14/4703* (2013.01); *A61K 38/00* (2013.01)

(58) Field of Classification Search
CPC ................................................ C07K 14/4738
See application file for complete search history.

(56) References Cited

U.S. PATENT DOCUMENTS 8,110,653 B2  2/2012 Stumpp et al.
2010/0305041 A1  12/2010 Jo et al.

OTHER PUBLICATIONS

Yuan et. al., "Tumor suppressor INK4: Refinement of $p16^{INK4A}$ structure and determination of $p15^{INK4B}$ structure by comparative modeling and NMR data", *Protein Science*, 9: 1120-1128 (2000).

*Primary Examiner* — Amber D Steele
(74) *Attorney, Agent, or Firm* — Leydig, Voit & Mayer, Ltd.

(57) ABSTRACT

A p15 protein variant; a polynucleotide encoding the p15 protein variant; a method for preparing the p15 protein variant; a pharmaceutical composition comprising the p15 protein variant; and a method for preventing and/or treating cancer comprising administering the p15 protein variant to a subject.

20 Claims, 9 Drawing Sheets

FIG. 4

```
3HG0_DArpin    MRGSHHHHHHGSDLGKKLLEAARAGQDDEVRILMANGADVNAEDKVGLTPLHLAAMNGHL
human_p15      MREENKGMPSGGGSDEGLASAAARGLYEKVRQLLEAGADPNGVNRFGRRAIQVMMMG-SA
               *  . :: **      ***   *  ::      ** * ** :*: ** ::: : ::

3HG0_DArpin    EIVEVLLKNGADVNAIDAIGT-PLHLVAMYGHLEIVEVLLKHGADVNAQDKFGKTAPDI
human_p15      RVAELLLHGAEPNCADPATLTRPVHDAAREGFLDTLVYLHRAGARLDVRIDAWGRLPVDL
               .: *:**::**  * *   *   :*  *  .:: :* *:: *: :: *    * *.*:

3HG0_DArpin    SINGNEDLAEILQKLN--             (SEQ ID NO: 7)
human_p15      AEERGHRDVAGYLRATGD             (SEQ ID NO: 1)
               : . :.* *  :::
```

FIG. 9

```
sp|P55271|CDN2B_MOUSE  ----------MLGGGSSDAGLATAAARGQVETVRQLLEAGADPNALNRFGRRP
sp|P55272|CDN2B_RAT    ----------MLGGGSSDAGLATAAARGQVETVRQLLEAGADPNAVNRFGRAP
sp|P42772|CDN2B_HUMAN  MREENKGMPSGGGSDEGLASAAARGLVEKVRQLLEAGADPNGVNRFGRRA
                                   *. .***  ****:******  **.,********* .******.

sp|P55271|CDN2B_MOUSE  IQVMMMGSAQVAELLLLHGAEPNCADPATLTRPVHDAAREGFLDTIVVLH
sp|P55272|CDN2B_RAT    IQVMMMGSAQVAELLLLHGAEPNCADPATLTRPVHDAAREGFLDTLMVLH
sp|P42772|CDN2B_HUMAN  IQVMMMGSARVAELLLLHGAEPNCADPATLTRPVHDAAREGFLDTILVLH
                       ******::************************************* sp|P55271|CDN2B_MOUSE  RAGARLDVCDAWGRLPVDLAEEQGHRDIARYLHAATGD  (SEQ ID NO: 4)
sp|P55272|CDN2B_RAT    RAGARLDVCDAWGRLPVDLAEEQGHRDIARYLHAATGD  (SEQ ID NO: 5)
sp|P42772|CDN2B_HUMAN  RAGARLDVRDAWGRLPVDLAEERGHRDVAGYLRTATGD  (SEQ ID NO: 1)
                       ******** ************* ****:  **  ****
```

P15 PROTEIN VARIANT AND USE THEREOF FOR PREVENTING OR TREATING CANCER

CROSS-REFERENCE TO RELATED APPLICATIONS

This application claims the benefit of Korean Patent Application No. 10-2014-0013239 filed on Feb. 5, 2014 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 29,797 bytes ASCII (Text) file named "719240_ST25.TXT," created Feb. 5, 2015.

BACKGROUND OF THE INVENTION

1. Field

Provided is a p15 protein variant; a polynucleotide encoding the p15 protein variant; a method for preparing the p15 protein variant; a pharmaceutical composition comprising the p15 protein variant; and a method for preventing and/or treating cancer comprising administering the p15 protein variant to a subject.

2. Description of the Related Art p15$^{INK4b}$ (hereinafter abbreviated as "p15") plays an important role in cell cycle regulation by decelerating the cell-cycle progression from the gap one phase ($G_1$) to the DNA synthesis (S) phase (i.e., $G_1 \rightarrow S$), a major check point (restriction point) responsible for the division of both normal and cancer cells. More specifically, p15 protein binds to cyclin-dependent kinase 4/6 (Cdk4/6) to arrest the cell proliferation (see, FIG. 1).

When p15 protein binds to Cdk4/6, the cell cycle progression from $G_1$ phase to S phase ($G_1 \rightarrow S$) is restricted, which, in turn, prohibits the subsequent events for cancer development including DNA synthesis in S phase and infinite cell division. Therefore, p15 protein can be effectively used as a tumor suppressor.

For cancer therapy using a p15 protein, it is required to provide a recombinant p15 protein having improved properties such as cell membrane permeability for delivering the protein into a cancer cell. However, expression of human p15 protein in *E. coli* cells presents problems The production of p15 protein is expressed in an insoluble form and exhibits low solubility and high flexibility (Yuan, C., et. al., 2000 Protein Science 1120-1128).

Thus, there is a need for a p15 protein variant with improved solubility that retains affinity to Cdk4/6, to provide for the effective application of p15 in cancer therapy.

BRIEF SUMMARY OF THE INVENTION

An embodiment provides a p15 protein variant. The p15 protein variant may have improved water-solubility as compared to native human p15, while retaining affinity to Cdk4/6. In one embodiment, the p15 protein variant comprises a substitution wherein at least one hydrophobic amino acid residue that is exposed on the tertiary structure of a p15 protein is substituted with a hydrophilic amino acid. In another embodiment, the p15 protein comprises a variant of SEQ ID NO: 1, 4, or 5 in which at least one exposed hydrophobic amino acid residue on the tertiary structure of a p15 protein is substituted with a hydrophilic amino acid.

Another embodiment provides a polynucleotide encoding the p15 protein variant.

Another embodiment provides a pharmaceutical composition including the p15 protein variant as an active ingredient.

Another embodiment provides a method of preventing and/or treating cancer, including administering the p15 protein variant to a subject in need thereof.

Another embodiment provides a method of preparing a p15 protein variant, by providing a polypeptide having a variant of a p15 amino acid sequence in which amino acid residues exposed externally on the three-dimensional structure of p15 protein are substituted.

BRIEF DESCRIPTION OF THE DRAWINGS

FIG. 4 illustrates amino acid sequence alignment of human p15 protein and DARPin 3HG0 based on secondary structural (mainly α-helix) position of the proteins.

FIG. 9 is a comparison of the amino acid sequences of human p15 protein, mouse p15 protein and rat p15 protein.

DETAILED DESCRIPTION OF THE INVENTION

Figure 1:
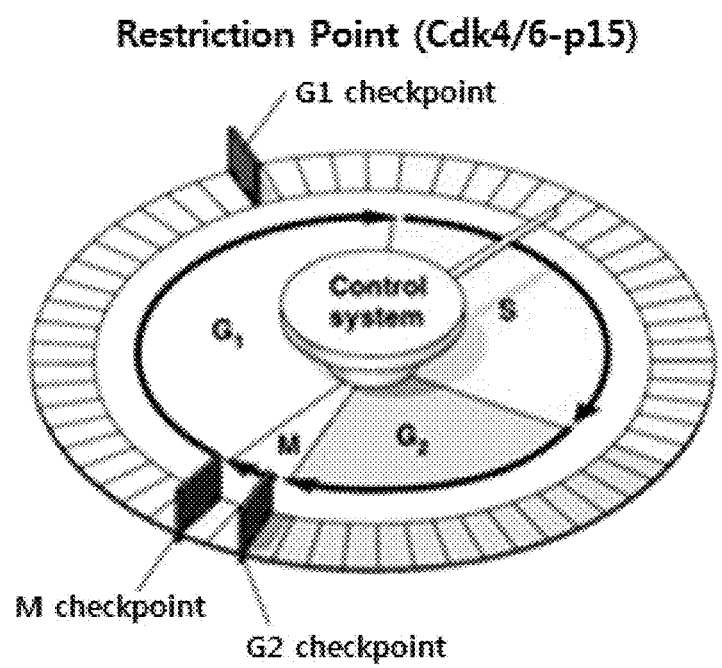
FIG. 1 is a schematic illustrating the cell cycle and three check points.

Intensive and thorough research into the application of p15 to cancer therapy resulted in the finding that: when an amino acid at a position such that it is exposed externally on the three-dimensional structure of p15 and is not responsible for binding to Cdk4/6 is substituted by a hydrophilic amino acid residue, the resulting p15 protein variant is improved in solubility, with the retention of affinity for Cdk4/6.

An embodiment provides a p15 protein variant. The p15 protein variant is characterized by an improvement in solubility, with the retention of affinity for Cdk4/6, through a mutation (e.g., substitution) on at least one selected from amino acids at such positions that they are exposed externally (e.g., to aqueous environment) on the three dimensional structure of the intact protein and not responsible for binding to Cdk4/6. For example, the p15 protein variant may comprise substitution of at least one hydrophobic amino acid that is externally exposed on the three dimensional structure of the protein independently with a hydrophilic amino acid.

The p15 protein variant may be non-naturally occurring. For example, the p15 protein variant may be synthetic or recombinant.

p15 is a cyclin-dependent kinase (CDK) inhibitor functioning to arrest the cell cycle by inactivating CDKs that phosphorylate retinoblastoma protein (Rb). With this function, p15 contributes to prevent the infinite division of cells to the development of cancer cells, and therefor acts as a tumor suppressor.

The p15 protein may be originated from mammals including primates, such as humans, monkeys and the like; and rodents, such as mice, rat, and the like. For example, the p15 may be a human p15 protein (SEQ ID NO: 1; Accession No. P42772), a mouse p15 protein (SEQ ID NO: 4; Accession No. P55271), or a rat p15 protein (SEQ ID NO: 5; Accession No. P55272).

The p15 protein variant may be provided by mutation of at least one amino acid on the amino acid sequence of p15 protein; wherein the at least one amino acid is a hydrophobic residue at a position externally exposed on the three dimensional structure of the protein in aqueous solution and is not responsible for binding to CDKs (e.g., Cdk4/6). The term "position externally exposed on the three dimensional structure of the protein" may refer to a position of the protein in aqueous solution in contact with a solvent (e.g., an aqueous solvent) or aqueous environment when the protein is formulated or administered into a body. The aqueous solvent may be any aqueous material, and for example, it may be, but not be limited to, water, an aqueous buffer solution (e.g., phosphate buffer saline (pH 7 to 8, pH 7.3 to 7.5, or pH 7.4), aqueous saline solution (e.g., with a concentration of about 0.9% (w/v) of NaCl or an osmotic pressure of about 300 mOsm/L), or a combination thereof, and the aqueous solution may refer to any solution comprising an aqueous solvent as described above. As used herein, the term "mutation" employed in association with amino acid sequences of p15 may refer to substitution of at least one amino acid with a different (e.g. hydrophilic) amino acid(s), for example, a change from a hydrophobic amino acid(s) to a hydrophilic amino acid(s), wherein the hydrophobic amino acid may be selected from the group consisting of leucine, cysteine, valine, phenyl alanine, tryptophan, isoleucine, proline, methionine, and a combination thereof, and the hydrophilic amino acid is selected from the group consisting of lysine (K), aspartic acid (D), glutamic acid (E), glutamine (Q), asparagine (N), serine (S), alanine (A), threonine (T), arginine (R), and a combination thereof.

In an embodiment, the p15 protein variant may consist of about 80 to about 250 amino acids or about 110 to about 150 amino acids, for example, about 138 amino acids or about 130 amino acids, and comprise or consisting essentially of a polypeptide of SEQ ID NO: 22. The polypeptide of SEQ ID NO: 22 may have an amino acid sequence identity of at least about 60%, at least about 65%, at least about 70%, at least about 75%, at least about 80%, at least about 85%, or at least about 90%, with a part of a wild-type p15 protein (e.g., a region of positions 67 to 115 of human p15 protein (SEQ ID NO: 1) or a region of positions 59 to 107 of a mouse wild-type p15 protein (SEQ ID NO: 4) or rat wild-type p15 protein (SEQ ID NO: 5)). In the p15 protein variant comprising SEQ ID NO: 22, the remaining part except the polypeptide of SEQ ID NO: 22 may comprise or consist essentially of any amino acids, for example, the amino acids identical (about 100%) to the corresponding region of a wild-type p15 protein; that is, the p15 protein variant may be obtained by substituting the region of positions 67 to 115 of human p15 protein of SEQ ID NO: 1 or the region of positions 59 to 107 of a mouse wild-type p15 protein of SEQ ID NO: 4 or rat wild-type p15 protein of SEQ ID NO: 5, with SEQ ID NO: 22.

[SEQ ID NO: 22]
X₁HGAEPNX₂AD PATX₃TRPVHD AAREGFLDTL X₄VLHX₅AGARL

DX₆X₇DAWGRX₈ wherein,

X₁, which corresponds to leucine at position 67 (L67) of SEQ ID NO: 1 or at position 59 (L59) of SEQ ID NO: 4 or SEQ ID NO: 5, is a hydrophilic amino acid or leucine (L), for example, lysine (K), arginine (R), aspartic acid (D), glutamic acid (E), glutamine (Q), asparagine (N), serine (S), or leucine (L), X₂, which corresponds to cysteine at position 74 (C74) of SEQ ID NO: 1 or at position 66 (C66) of SEQ ID NO: 4 or SEQ ID NO: 5, is a hydrophilic amino acid or cysteine (C), for example, serine (S) or cysteine (C);

X₃, which corresponds to leucine at position 80 (L80) of SEQ ID NO: 1 or at position 72 (L72) of SEQ ID NO: 4 or SEQ ID NO: 5, is a hydrophilic amino acid or leucine (L), for example, serine (S), arginine (R), lysine (K), aspartic acid (D), glutamic acid (E), glutamine (Q), asparagine (N), or leucine (L);

X₄ is valine (V) or methionine (M);

X₅ is arginine (R) or lysine (K);

X₆, which corresponds to valine at position 108 (V108) of SEQ ID NO: 1 or at position 100 (V100) of SEQ ID NO: 4 or SEQ ID NO: 5, is a hydrophilic amino acid or valine (V), for example, alanine (A), aspartic acid (D), glutamic acid (E), glutamine (Q), asparagine (N), or valine (V);

X₇ is arginine (R) or cysteine (C); and

X₈, which corresponds to leucine at position 115 (L115) of SEQ ID NO: 1 or at position 107 (L107) of SEQ ID NO: 4 or SEQ ID NO: 5, is a hydrophilic amino acid, leucine (L), for example, threonine (T), arginine (R), lysine (K), aspartic acid (D), glutamic acid (E), glutamine (Q), asparagine (N), serine (S), or leucine (L).

In SEQ ID NO: 22, the hydrophilic amino acid is selected from the group consisting of lysine (K), aspartic acid (D), glutamic acid (E), glutamine (Q), asparagine (N), serine (S), alanine (A), threonine (T), arginine (R), and a combination thereof. In addition, in SEQ ID NO: 22, at least one of X₁, X₂, X₃, X₆, and X₈ is independently selected from hydrophilic amino acids as listed above, for example, including serine (S), lysine (K), aspartic acid (D), glutamic acid (E), glutamine (Q), asparagine (N), alanine (A), threonine (T), and arginine (R), for example, including serine (S), lysine (K), alanine (A), or threonine (T) (e.g., X₁ is lysine (K), arginine (R), aspartic acid (D), glutamic acid (E), glutamine (Q), asparagine (N), or serine (S); and/or X₂ is serine (S); and/or X₃ is serine (S), arginine (R), lysine (K), aspartic acid (D), glutamic acid (E), glutamine (Q), or asparagine (N); and/or X₆ is alanine (A), aspartic acid (D), glutamic acid (E), glutamine (Q), or asparagine (N); and/or X₈ is threonine (T), arginine (R), lysine (K), aspartic acid (D), glutamic acid (E), glutamine (Q), asparagine (N), or serine (S), as described above).

On a wild-type p15 protein, for example, the human p15 protein comprising the amino acid sequence of SEQ ID NO: 1, the amino acid position to undergo such mutation (e.g., substitution) may be at least one selected from the group consisting of leucine at position 67 (L67), cysteine at position 74 (C74), leucine at position 80 (L80), valine at position 108 (V108), and leucine at position 115 (L115).

Amino acid residues to be substituted on the amino acid sequence of SEQ ID NO: 1 are as follows:

```
Wild-Type Human p15 (SEQ ID NO: 1; Accession No.
P42772)
MREENKGMPS GGGSDEGLAS AAARGLVEKV RQLLEAGADP

NGVNRFGRRA IQVMMMGSAR VAELLLLHGA EPNCADPATL

TRPVHDAARE GFLDTLVVLH RAGARLDVRD AWGRLPVDLA

EERGHRDVAG YLRTATGD
```

(possible amino acid residues to undergo substitution are shown in bold and underline)

The amino acid to be substituted on the human P15 protein may be at least one selected from the group consisting of leucine at position 67 (L67), cysteine at position 74 (C74), leucine at position 80 (L80), valine at position 108 (V108), and leucine at position 115 (L115), or any combination thereof.

These amino acids are hydrophobic residues exposed externally (i.e., to the solvent) on the three-dimensional structure of p15 protein, and may be substituted with negatively or positively charged amino acids or polar amino acids. The solvent may be any aqueous solvent, and for example, it may be, but not be limited to, water, a aqueous buffer solution (e.g., phosphate buffer saline (pH 7 to 8, pH 7.3 to 7.5, or pH 7.4), aqueous saline solution (e.g., with a concentration of about 0.9% (w/v) of NaCl or an osmotic pressure of about 300 mOsm/L), or a combination thereof.

The p15 protein variant may be prepared by independently substituting at least one of the above amino acid residues of SEQ ID NO: 1, that is, leucine at position 67 (L67), cysteine at position 74 (C74), leucine at position 80 (L80), valine at position 108 (V108), and leucine at position 115 (L115), independently with lysine (K), aspartic acid (D), glutamic acid (E), glutamine (Q), asparagine (N), serine (S), alanine (A), threonine (T), or arginine (R).

For example, the p15 protein variant may comprise at least one of the following mutations:
a substitution of leucine at position 67 (L67) of SEQ ID NO: 1 with lysine (K), arginine (R), aspartic acid (D), glutamic acid (E), glutamine (Q), asparagine (N), or serine (S),
a substitution of cysteine at position 74 (C74) of SEQ ID NO: 1 with serine (S),
a substitution of leucine at position 80 (L80) of SEQ ID NO: 1 with serine (S), arginine (R), lysine (K), aspartic acid (D), glutamic acid (E), glutamine (Q), or asparagine (N),
a substitution of valine at position 108 (V108) of SEQ ID NO: 1 with alanine (A), aspartic acid (D), glutamic acid (E), glutamine (Q), or asparagine (N), and
a substitution of leucine at position 115 (L115) of SEQ ID NO: 1 with threonine (T), arginine (R), lysine (K), aspartic acid (D), glutamic acid (E), glutamine (Q), asparagine (N), or serine (S).

In a further embodiment, the p15 protein variant may comprise SEQ ID NO: 1 containing all the following substitutions: a substitution of leucine at position 67 (L67) with lysine (K), arginine (R), aspartic acid (D), glutamic acid (E), glutamine (Q), asparagine (N), or serine (S), a substitution of cysteine at position 74(C74) with serine (S), a substitution of leucine at position 80 (L80) with serine (S), arginine (R), lysine (K), aspartic acid (D), glutamic acid (E), glutamine (Q), or asparagine (N), a substitution of valine at position 108 (V108) with alanine (A), aspartic acid (D), glutamic acid (E), glutamine (Q), or asparagine (N), and a substitution of leucine at position 115 (L115) with threonine (T), arginine (R), lysine (K), aspartic acid (D), glutamic acid (E), glutamine (Q), asparagine (N), or serine (S). For instance the p15 protein variant can comprise or consist essentially of SEQ ID NO: 2.

```
Human p15 variant
                                    (SEQ ID NO: 2)
MREENKGMPS GGGSDEGLAS AAARGLVEKV RQLLEAGADP

NGVNRFGRRA IQVMMMGSAR VAELLLKHGA EPNSADPATS

TRPVHDAARE GFLDTLVVLH RAGARLDARD AWGRTPVDLA

EERGHRDVAG YLRTATGD
```

(substituted amino acid residues are shown in bold and underline)

Alignment of amino acid sequences of p15 proteins from sources other than humans, for example, mouse p15 protein (SEQ ID NO: 4) or rat p15 protein (SEQ ID NO: 5) with the amino acid sequence of human p15 protein shows that residues at positions 59, 66, 72, 100 and 107 (corresponding to positions 67, 74, 80, 108, and 107, respectively, on the amino acid sequence of SEQ ID NO: 1) are exposed externally on the three dimensional structure in contact with an aqueous solvent (see FIG. 9).

Another embodiment provides a p15 protein variant comprising a substitution of at least one of amino acids at positions 59, 66, 72, 100 and 107 on the amino acid sequence of SEQ ID NO: 4 or SEQ ID NO: 5 independently with lysine (K), aspartic acid (D), glutamic acid (E), glutamine (Q), asparagine (N), serine (S), alanine (A), threonine (T), or arginine (R). For example, the p15 protein variant may comprise at least one selected from the group consisting of:
a substitution of the amino acid (leucine) at position 59 (L59) on the amino acid sequence of SEQ ID NO: 4 or SEQ ID NO: 5 with lysine (K), arginine (R), aspartic acid (D), glutamic acid (E), glutamine (Q), asparagine (N), or serine (S), or,
a substitution of the amino acid (cysteine) at position 66 (C66) on the amino acid sequence of SEQ ID NO: 4 or SEQ ID NO: 5 with serine (S),
a substitution of the amino acid (leucine) at position 72 (L72) on the amino acid sequence of SEQ ID NO: 4 or SEQ ID NO: 5 with serine (S), arginine (R), lysine (K), aspartic acid (D), glutamic acid (E), glutamine (Q), or asparagine (N),
a substitution of the amino acid (valine) at position 100 (V100) on the amino acid sequence of SEQ ID NO: 4 or SEQ ID NO: 5 with alanine (A), aspartic acid (D), glutamic acid (E), glutamine (Q), or asparagine (N), and
a substitution of the amino acid (leucine) at position 107 (L107) on the amino acid sequence of SEQ ID NO: 4 or SEQ ID NO: 5 with threonine (T), arginine (R), lysine (K), aspartic acid (D), glutamic acid (E), glutamine (Q), asparagine (N), or serine (S).

Another embodiment provides a polynucleotide encoding the p15 protein variant, a recombinant vector carrying (comprising) the polynucleotide, and a recombinant cell harboring (comprising) the recombinant vector.

The polynucleotide encoding the p15 protein variant may encode the amino acid sequence of SEQ ID NO: 2. For example, the polynucleotide may comprise the nucleotide sequence of SEQ ID NO: 3 (417 bp; GC content: 69%).

As used herein, the term "vector" refers to a means for expressing a gene of interest in a host cell, as exemplified by a plasmid vector, a cosmid vector, and a viral vector, such as a bacteriophage vector, an adenovirus vector, a retrovirus vector and an adeno-associated virus vector. The recombinant vector may be constructed from well-known plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λΔz1, M13, etc.) or viruses (for example, SV40, etc.) by known manipulation (genetic engineering) techniques.

In the recombinant vector, the polynucleotide encoding the protein conjugate may be operatively linked to a promoter. The term "operatively linked" is intended to pertain to a functional linkage between a nucleotide sequence of interest and an expression regulatory element (for example, a promoter sequence) so that the expression of the nucleotide sequence of interest is governed by the regulatory element. For instance, when it is "operatively linked" to the regulatory element, the nucleotide sequence of interest can be transcribed and/or translated under the control of the regulatory element.

The recombinant vector may be typically constructed as a cloning vector or an expression vector. For recombinant expression vectors, a vector typically available for expressing a foreign protein in plant, animal or microorganism cells may be employed. Various methods well known in the art may be used for the construction of recombinant vectors.

For use in hosts, such as prokaryotic or eukaryotic cells, the recombinant vector may be constructed appropriately. For example, when a vector is constructed as an expression vector for use in a prokaryotic host, the vector typically includes a strong promoter for transcription (e.g., a $pL^\lambda$ promoter, a CMV promoter, a trp promoter, a lac promoter, a tac promoter, a T7 promoter, etc.), a ribosomal binding side for initiating translation, and transcriptional/translational termination sites. On the other hand, an expression vector for use in a eukaryotic host includes an origin of replication operable in a eukaryotic cell, such as, but not limited to, an f1 origin of replication, an SV40 origin of replication, a pMB1 origin of replication, an adeno origin of replication, an AAV origin of replication, a BBV origin of replication. In addition, the expression vector typically includes a promoter derived from mammalian cells (for example, metallothionein promoter) or from mammalian viruses (for example, adenovirus late promoter, vaccinia virus 7.5K promoter, SV40 promoter, cytomegalovirus promoter and tk promoter of HSV), and a polyadenylation sequence as a transcription termination sequence.

The recombinant cell may be prepared by introducing the recombinant vector into a suitable host cell. So long as it allows for the sequential cloning and expression of the recombinant vector in a stable manner, any host cell known in the art may be employed. Examples of the prokaryotic host cell available may be at least one selected from the group consisting of *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium, Serratia marcescens*, and various *Pseudomonas* species. Eukaryotic host cells to be transformed may be at least one selected from the group consisting of *Saccharomyce cerevisiae*, insect cells, plant cells and animal cells including Sp2/0, CHO (Chinese hamster ovary) K1, CHO DG44, PER.C6, W138, BHK, COS-7, 293, HepG2, Huh7, 3T3, RIN, and MDCK, but not be limited thereto.

Using a method well known in the art, the polynucleotide or a recombinant vector carrying the polynucleotide may be introduced (incorporated) into a host cell. This transformation is carried out through $CaCl_2$ or electroporation when the host cell is prokaryotic. For eukaryotic host cells, the genetic introduction may be achieved using, but not limited to, microinjection, calcium phosphate precipitation, electroporation, liposome-mediated transfection, or particle bombardment.

To select a (recombinant vector) transformed host cell, advantage may be taken of the phenotype attributed to a selection marker according to a method known in the art. For example, when the selection marker is a gene resistant to a certain antibiotic, the host cells may be grown in the presence of the antibiotic in a medium to select a transformant of interest.

In the p15 protein variant, the mutated amino acid residues are those that are hydrophobic with external exposure in the three-dimensional conformation of a wild type p15 protein and have influence on the solubility of the protein in contact with an aqueous solvent. The p15 protein variant is improved in solubility compared to the wild-type p15 protein because at least one of the externally exposed, hydrophobic residues is substituted by a hydrophilic amino acid, such as an electrically charged amino acid or a polar amino acid. This improvement in protein solubility prevents the p15 protein variant from precipitating upon expression or purification, which leads to increasing the expression of the protein (or the external secretion of the protein). Given an increase in solubility, the p15 protein variant is improved in stability upon formulation and/or storage, and thus can maintain its effective delivery at a high level in vivo upon administration. Additionally, because the amino acid residues which are mutated exist at positions not responsible for binding to Cdk4/6, the p15 protein variant retains affinity for CDKs such as Cdk4/6 at the same level as that of the wild-type p15 and thus functions normally to regulate the cell cycle. In some embodiments, the p15 protein variant is advantageous for mass production thanks to improvement in expression level in host cells, and exhibits such high stability that it can be delivered in an elevated amount in vivo upon administration. In addition, the p15 protein variant retains affinity for CDKs sufficiently to regulate the cell cycle and thus to exert inhibitory activity against cancer by infinite cell division. Hence, the p15 protein variant serves as an effective and potent anticancer agent.

Another embodiment provides a pharmaceutical composition comprising the p15 protein variant as an active ingredient. The pharmaceutical composition is useful for the preventing and/or treating cancer.

Another embodiment provides a method of preventing and/or treating cancer, comprising administering the p15 protein variant to a subject in need thereof. The p15 protein variant may be used in a pharmaceutically effective amount, which amount may be determined by the skilled medical practitioner or medical researcher. This method may further comprise identifying the subject is in need of the prevention and/or treatment of cancer, prior to the administration. The step of identifying a subject in need may be conducted by any manner and/or method known to relevant field for identifying whether or not a subject needs the prevention and/or treatment of cancer. For example, the step of identifying the subject in need may include diagnosing a subject to have a cancer, or identifying a subject who is diagnosed as a cancer patient.

The pharmaceutical composition may further comprise a pharmaceutical additive, such as a carrier, a diluent and/or an excipient in addition to the p15 protein variant.

A pharmaceutically acceptable carrier which is typically used for drug formulations may be available for the pharmaceutical composition. Examples of the carrier include lactose, dextrose, sucrose, sorbitol, mannitol, starch, *acacia* gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, but are not limited thereto. In addition, the pharmaceutical composition may further comprise at least one selected from the group consisting of a diluent, an excipient, a lubricant, a humectant, a sweetener, a flavoring agent, an emulsifier, a suspending agent, and a preservative.

The pharmaceutical composition may be administered orally or parenterally. For parenteral administration, the administration may be carried out via intravenous, subcutaneous, intramuscular, intraperitoneal, intradermal, local, intranasal, intrapulmonary, and intrarectal routes, but is not limited thereto. For oral administration, however, the pharmaceutical composition is preferably coated or formulated to protect the active ingredient from being degraded in the stomach because proteins or peptides are digested by pepsin. In addition, the administration may be performed with the aid of an instrument adapted for delivering the pharmaceutical composition to target cells.

A dose of the p15 protein variant in the pharmaceutical composition may vary depending on various factors including the type of formulation; the patient's age, weight, and sex; the severity of the disorder being treated; diet; the time of administration; the route of administration; the rate of excretion; and sensitivity. For example, the pharmaceutically effective amount of the active ingredient in the pharmaceutical composition may range in daily dose from about 0.001 to about 1,000 mg/kg, particularly from about 0.01 to about 100 mg/kg, and more particularly from about 0.1 to about 50 mg/kg, but is not limited thereto. The daily dose may be formulated into a unit dose form or distributed into separate dose forms, or may be included within a multiple dose package. As used herein, the term "pharmaceutically effective amount" refers to an amount at which the active ingredient can exert a desired effect, and may fall within the range set forth above.

The pharmaceutical composition may be formulated into: solutions in oil or aqueous media, suspensions, syrup, emulsions, elixirs, powders, granules, tablets, or capsules, and in this context, a dispersant or a stabilizer may be further employed.

The subject may be intended to encompass all animals that need the delivery of the cytotoxic drug to or into a cancer (tumor) cell, and cells derived (originated or isolated) therefrom. For example, all mammals including primates such as humans and monkeys, and rodents such as mice and rats, cells or tissues derived (originated or isolated) therefrom, and cultures of the cells or tissues may fall into the scope of the subject. The subject may be a person suffering from cancer, or at risk of cancer, or cancer cells or tissues derived (originated or isolated) from the person, a culture thereof; or any combination thereof.

The cancer may be related to the aberrant function of p15. The cancer may be solid cancer or blood cancer. Examples of the cancer include squamous cell carcinoma, small-cell lung cancer, non-small-cell lung cancer, adrenocarcinoma of lung, squamous cell carcinoma of lung, peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, or any combination thereof. The cancer may be primary or metastatic cancer.

With regard to the prophylactic and/or therapeutic effect on cancer, the composition suppresses cancer cells from undergoing migration, invasion and/or metastasis, in addition to inhibiting the growth of primary cancer cells. Therefore, the composition not only inhibits cancer cell growth, but also suppresses the malignancy of cancer due to migration, invasion and metastasis.

Another embodiment provides a method of preparing a p15 protein variant having increased solubility or a method of increasing solubility of p15 protein, comprising mutating (e.g., substituting) at least one of hydrophobic amino acid residues externally exposed on a three-dimensional structure of p15 with a different amino acid.

As described above, a hydrophobic amino acid residue exposed externally on the 3-dimensional structure of p15 may be in contact with an aqueous solvent and located at a position that is not involved in the binding of CDKs (e.g., Cdk4/6). The hydrophobic amino acid residue may be at least one selected from the group consisting of leucine at position 67 (L67), cysteine at position 74 (C74), leucine at position 80 (L80), valine at position 108 (V108), and leucine at position 115 (L115), or any combination thereof; on the amino acid sequence of SEQ ID NO: 1.

The mutation may be a substitution of at least one of the amino acid residues with a different amino acid. For example, the mutation may be conducted by substituting at least one selected from the group consisting of leucine at position 67 (L67), cysteine at position 74 (C74), leucine at position 80 (L80), valine at position 108 (V108), and leucine at position 115 (L115) on the amino acid sequence of SEQ ID NO: 1, independently with lysine (K), aspartic acid (D), glutamic acid (E), glutamine (Q), asparagine (N), serine (S), alanine (A), threonine (T), or arginine (R).

The method of preparing the p15 protein variant can comprise providing a polypeptide having the amino acid sequence described above (e.g., SEQ ID NO: 1, 4, or 5 having the described substitutions). The polypeptide can be provided by any suitable method, such as by expressing a polynucleotide encoding the polypeptide in a cell, whereby the polypeptide is produced. Alternatively, the polypeptide may be synthesized using well-known protein synthesis techniques.

The method for preparing a p15 protein variant having increased solubility or increasing solubility of p15 protein may comprise carrying out at least one substitution of an amino acid of SEQ ID NO: 1 selected from the group consisting of:

substitution of leucine at position 67 (L67) on the amino acid sequence of SEQ ID NO: 1 with lysine (K), arginine (R), aspartic acid (D), glutamic acid (E), glutamine (Q), asparagine (N), or serine (S), substitution of cysteine at position 74 (C74) on the amino acid sequence of SEQ ID NO: 1 with serine (S), substitution of leucine at position 80 (L80) on the amino acid sequence of SEQ ID NO: 1 with serine (S), arginine (R), lysine (K), aspartic acid (D), glutamic acid (E), glutamine (Q), or asparagine (N), substitution of valine at position 108 (V108) on the amino acid sequence of SEQ ID NO: 1 with alanine (A), aspartic acid (D), glutamic acid (E), glutamine (Q), or asparagine (N), and substitution of leucine at position 115 (L115) on the amino acid sequence of SEQ ID NO: 1 with threonine (T), arginine (R), lysine (K), aspartic acid (D), glutamic acid (E), glutamine (Q), asparagine (N), or serine (S).

In mouse p15 protein (SEQ ID NO: 4) and rat p15 protein (SEQ ID NO: 5), the hydrophobic amino acid residue exposed externally on the 3-dimensional structure of p15 and located at a position irrelevant to the binding site of CDKs (for example, Cdk4/6) may be at least one selected from the group consisting of leucine at positions 59 (L59) (corresponding to L67 of SEQ ID NO: 1), cysteine at position 66 (C66) (corresponding to C74 of SEQ ID NO: 1), leucine at position 72 (L72)(corresponding to L80 of SEQ ID NO: 1), valine at position 100 (V100)(corresponding to V108 of SEQ ID NO: 1), and leucine at position 107 (L107) (corresponding to L115 of SEQ ID NO: 1). Therefore, the method of preparing a p15 protein variant having increased solubility or a method of increasing solubility of p15 protein may comprise substituting at least one selected from the above amino acids with different one. In a still further embodiment, the method of preparing a p15 protein variant having increased solubility or a method of increasing solubility of p15 protein may comprise substituting at least one selected from the group consisting of leucine at positions 59 (L59) (corresponding to L67 of SEQ ID NO: 1), cysteine at position 66 (C66)(corresponding to C74 of SEQ ID NO: 1), leucine at position 72 (L72)(corresponding to L80 of SEQ ID NO: 1), valine at position 100 (V100)(corresponding to V108 of SEQ ID NO: 1), and leucine at position 107 (L107) (corresponding to L115 of SEQ ID NO: 1), on the amino acid sequence of SEQ ID NO: 4 (mouse p15) or SEQ ID NO: 5 (rat p15), independently with lysine (K), aspartic acid (D), glutamic acid (E), glutamine (Q), asparagine (N), serine (S), alanine (A), threonine (T), or arginine (R).

For example, the method of preparing a p15 protein variant having increased solubility or a method of increasing solubility of p15 protein may comprise carrying out at least one substitution of an amino acid of SEQ ID NO: 4 or SEQ ID NO: 5 selected from the group consisting of:

substitution of leucine at position 59 (L59) on the amino acid sequence of SEQ ID NO: 4 or SEQ ID NO: 5 with lysine (K), arginine (R), aspartic acid (D), glutamic acid (E), glutamine (Q), asparagine (N), or serine (S), substitution of cysteine at position 66 (C66) on the amino acid sequence of SEQ ID NO: 4 or SEQ ID NO: 5 with serine (S), substitution of leucine at position 72 (L72) on the amino acid sequence of SEQ ID NO: 4 or SEQ ID NO: 5 with serine (S), arginine (R), lysine (K), aspartic acid (D), glutamic acid (E), glutamine (Q), or asparagine (N), substitution of valine at position 100 (V100) on the amino acid sequence of SEQ ID NO: 4 or SEQ ID NO: 5 with alanine (A), aspartic acid (D), glutamic acid (E), glutamine (Q), or asparagine (N), and substitution of leucine at position 107 (L107) on the amino acid sequence of SEQ ID NO: 4 or SEQ ID NO: 5 with threonine (T), arginine (R), lysine (K), aspartic acid (D), glutamic acid (E), glutamine (Q), asparagine (N), or serine (S).

The amino acid substitutions can be made using routine techniques, such as by mutating or otherwise preparing a polynucleotide sequence that encodes an amino acid sequence comprising the foregoing mutations.

The amino acids to be mutated according to one embodiment are hydrophobic with exposure to an aqueous external environment on the three-dimensional structure of p15 protein, and are located at positions not responsible for binding to CDKs (e.g., Cdk4/6). The hydrophobic amino acid residues exposed externally on the three-dimensional structure may be selected as suitable for amino acid substitution by comparing amino acid sequences, and/or secondary and/or tertiary structures between p15 protein and proteins with ankyrin repeat (ANK) repeat motif, wherein the ANK repeat motif not only exhibit a high expression level in host cells, such as E. coli, but also are highly soluble and similar in secondary or tertiary structure to a p15 protein. For example, the proteins with an ANK repeat motif which not only exhibit a high expression level in host cells, such as E. coli, but also are highly soluble and similar in secondary or tertiary structure to p15 protein may be selected from the group consisting of designed ankyrin repeat proteins (DARPins, examples of which include: PDB 3HG0; SEQ ID NO: 7).

Figure 2:
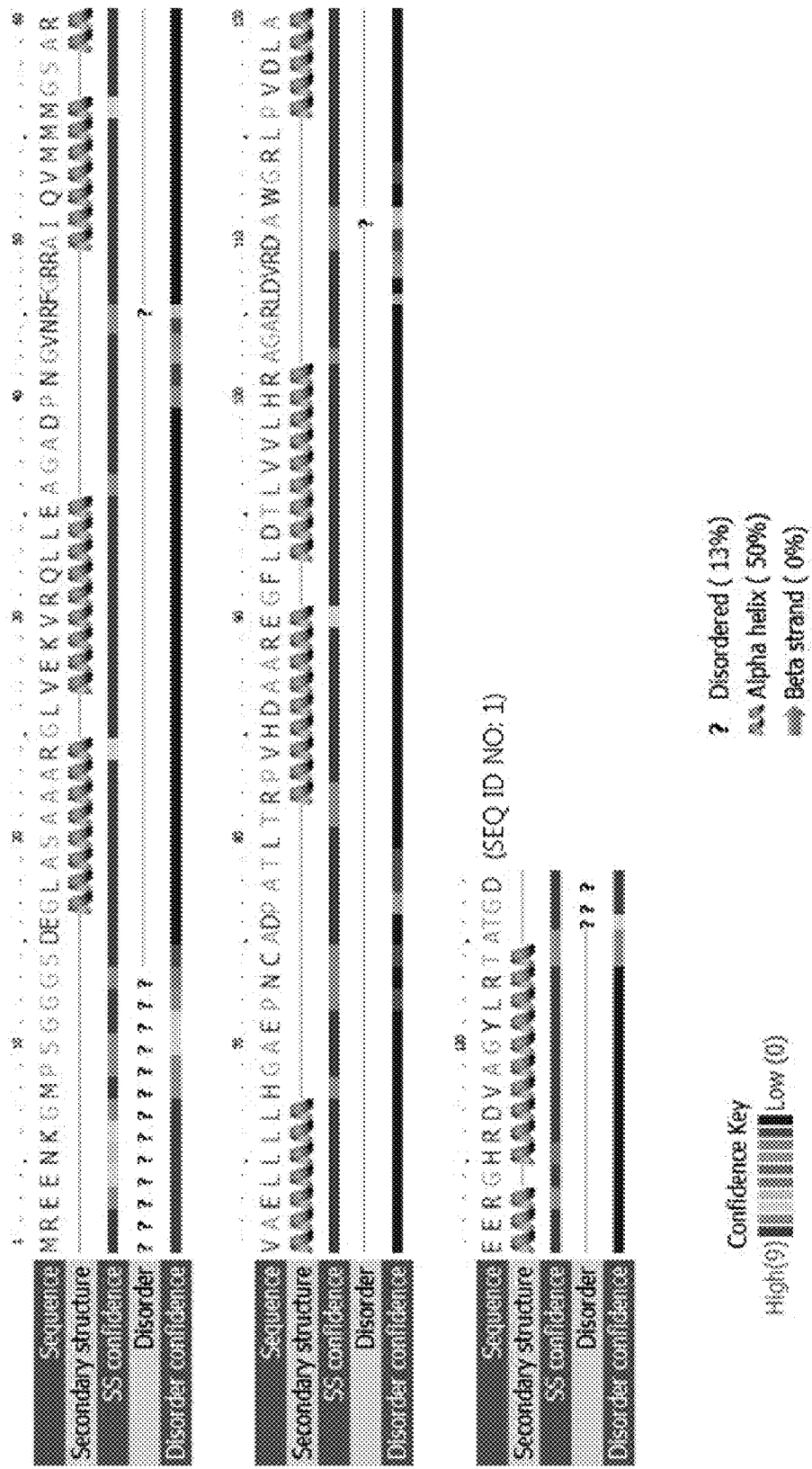
FIG. 2 illustrates secondary structural analysis of human p15 protein using the Phyre2 tool (Imperial College of London, Structural Bioinformatics Group, available online at <<www.sbg.bio.ic.ac.uk/phyre2/>>).
Figure 3:
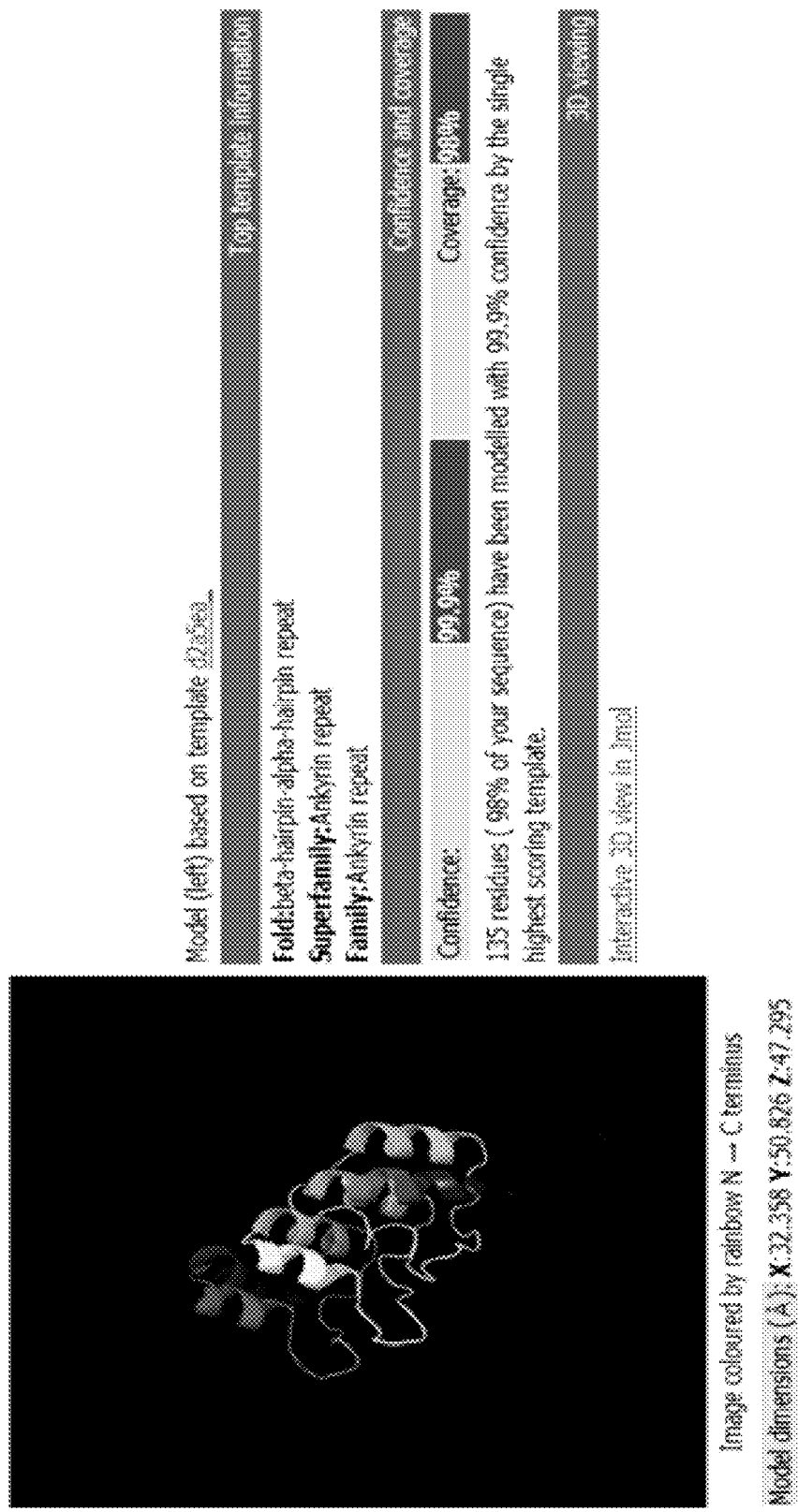
FIG. 3 illustrates tertiary structural modeling of human p15 protein using Phyre2 tool (Imperial College of London, Structural Bioinformatics Group, available online at <<www.sbg.bio.ic.ac.uk/phyre2/>>).

For example, the comparison of a secondary structure-based amino acid sequence alignment of human p15 protein (SEQ ID NO: 1) with DARPin PDB 3HG0 is shown in FIGS. 2-4.

More specifically, FIG. 2 shows the results of secondary structural analysis of human p15 protein using Phyre2 (http://www.sbg.biaic.ac.uk/phyre2/). FIG. 3 shows the results of tertiary structural modeling of human p15 protein using Phyre2 tool (Imperial College of London, Structural Bioinformatics Group, available online at <<www.sbg-.bio.ic.ac.uk/phyre2/>>).

According to the research of DALI database (http://ekhidna.biocenter.helsinki.fi/dali_server/), DARPin (PDB 3HG0) is found to have the most similar tertiary structure to human p15, and to exhibit improved solubility when it is expressed in E. coli. For these reasons, DARPin (PDB 3HG0) was selected to serve as a basis of comparison with p15 to determine the mutation point of p15 protein. FIG. 4 shows the results of amino acid sequence alignment of human p15 protein and DARPin 3HG0 based on a comparison of the secondary structural (mainly α-helix) position of protein.

Figure 5:
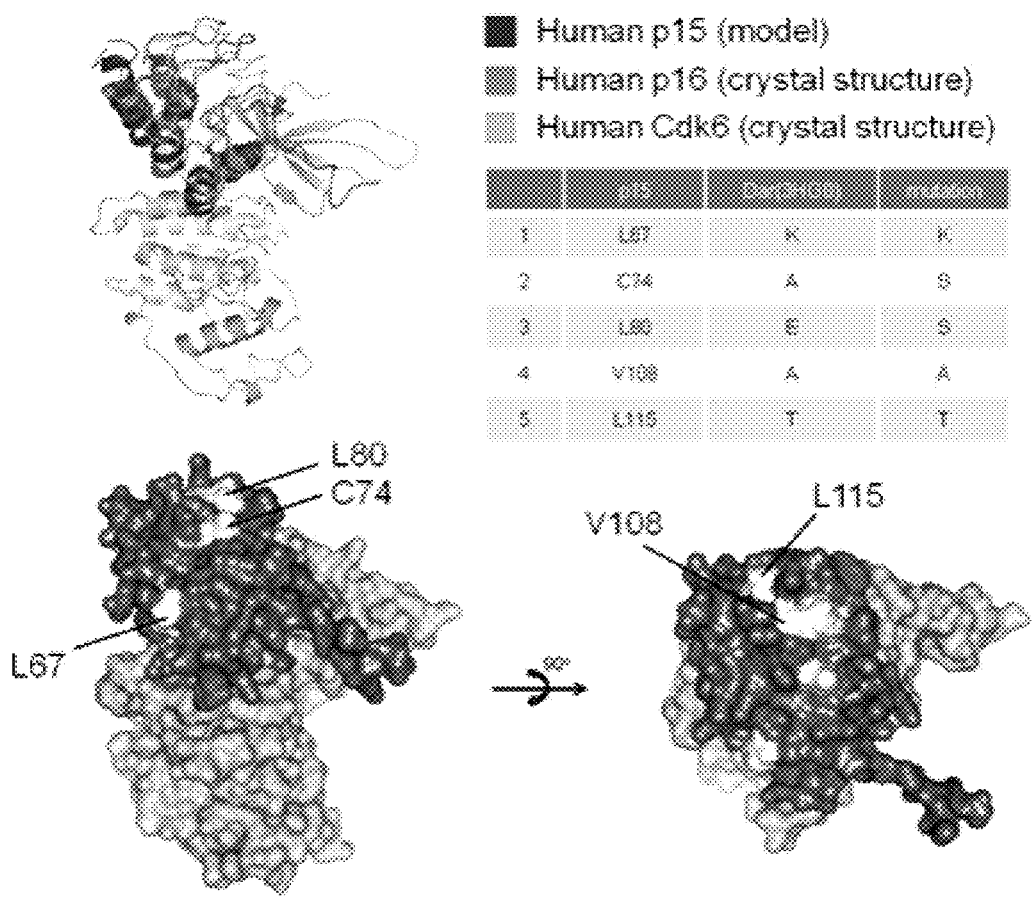
FIG. 5 is a schematic illustrating mutation points of human p15 protein resulted from the secondary or tertiary structural analysis shown in FIGS. 3 and 4.

FIG. 5 schematically displays the mutation points of human p15 protein determined through the secondary or tertiary structural analysis shown in FIGS. 3 and 4. The mutation points of p15 protein, which are determined through amino acid sequence analysis, secondary structure-based alignment, and tertiary structural analysis, are hydrophobic amino acid residues exposed to a solvent-exposed area and do not affect the binding with Cdk4/6.

Alignment of secondary or tertiary structure-based amino acid sequences between a protein of interest to be improved in solubility and a reference protein that is of high solubility and having similar secondary or tertiary structure to the protein of interest allows a person skilled in the art to locate (e.g., search for) search positions (e.g., hydrophobic residues) at which desirable mutations would be achieved, to increase the solubility (e.g., solubility is an aqueous solution) of the protein of interest (with the proviso that the amino acids are hydrophobic residues exposed to an aqueous solvent and are not responsible for the original function of the protein of interest). Substituting the hydrophobic amino acids at these positions with hydrophilic residues could increase the solubility of the protein of interest.

Another embodiment provides a method of analyzing secondary or tertiary structure of a protein of interest, and a method of providing information for increasing the solubility of a protein of interest or a method of increasing the solubility of a protein of interest using the method of analyzing secondary or tertiary structure of a protein of interest.

The method of analyzing secondary or tertiary structure of a protein of interest may comprise conducting secondary or tertiary structure-based amino acid sequence alignment of the protein of interest (e.g., p15) and a reference protein (e.g., a DARPin). The term "secondary or tertiary structure-based amino acid sequence alignment" may refer to comparison of amino acid sequences aligned on a secondary or tertiary structure between a protein of interest and a reference protein.

Any protein that is to be analyzed for its structure may be the protein of interest. For example, any biologically protein that is to be conferred with increased solubility, with the aim of improving its formulation stability and in vivo delivery efficiency may be the protein of interest. The protein of interest may be at least one anticancer protein selected from the group consisting of, but not limited to, INK4 lineage proteins (for example, p15 (INK4b; e.g., human p15 protein (Accession No. P42772), mouse p15 protein (Accession No. P55271), rat p15 protein (Accession No. P55272), etc.), p16 (INK4a; e.g., human p16 protein (Accession No. NP_000068; SEQ ID NO: 18), mouse p16 protein (Accession No. NP_001035744; SEQ ID NO: 20), rat p16 protein (SEQ ID NO: 21), etc.), p18 (INK4c; e.g., human p18 protein (Accession No. NP_001253), mouse p18 protein (Accession No. NP_031697), etc.), p19 (INK4d; e.g., human p19 protein (Accession No. NP_001791), mouse p19 protein (Accession No. NP_034008)), etc.), p53 (e.g., human p53 protein (Accession No. NP_000537), and mouse p53 protein (Accession No. NP_001120705, etc.), or any combination thereof.

The reference protein may be highly soluble and have a secondary or tertiary structure similar to that of a protein of interest. For ease in acquirement, the reference protein may be one expressed at a high efficiency in a host cell, such as E. coli. For example, the reference protein may be a protein with ANK repeat(s), for example, a DARPins.

DARPins are genetically engineered antibody mimetic proteins which exhibit high specificity and high binding-affinity to target protein. They are derived from natural ankyrin proteins and consist of at least two, usually three, four or five repeat motifs of these proteins. Their molecular mass is about 10, 14 or 18 kDa for three-, four- or five-repeat DARPins, respectively.

In one embodiment, a DARPin available for use as the reference protein may be selected from the group consisting of DARPins containing 4 ANK repeats (e.g., DARPin 3HGO, 2Y0B, 2XZT, 2XZD, 2V4H), DARPins containing 5-ANK repeats (e.g., DARPin 2Y1L, 2J85, 4DX6, 5V5Q, 4DRX, 2P2C, 3NOG), and a combination thereof.

Amino acid sequences of the DARPins available for use as reference proteins are given in Tables 1 and 2, below:

TABLE 1

DARPin containing 4 ANK repeats

| DARPin | Amino acid sequence |
| --- | --- |
| 3HGO | MRGSHHHHHHGSDLGKKLLEAARAGQDDEVRILMANGADVN<br>AEDKVGLTPLHLAAMNDHLEIVEVLLKNGADVNAIDAIGET<br>PLHLVAMYGHLEIVEVLLKHGADVNAQDKFGKTAFDISIDN<br>GNEDLAEILQKLN (SEQ ID NO: 7) |

TABLE 1-continued

DARPin containing 4 ANK repeats

| DARPin | Amino acid sequence |
| --- | --- |
| 2Y0B | MRGSHHHHHHGSDLGKKLLEATRAGQDDEVRILMANGADVN<br>AMDDAGVTPLHLAAKRGHLEIVEVLLKHGADVNARDIWGRT<br>PLHLAATVGHLEIVEVLLEYGADVNAQDKFGKTAFDISIDN<br>GNEDLAEILQKLN (SEQ ID NO: 8) |
| 2XZT | MRGSHHHHHHGSDLGKKLLEATRAGQDDEVRILMANGADVN<br>AMDDAGVTPLHLAAKRGHLEIVEVLLKHGADVNASDSWGRT<br>PLHLAATVGHLEIVEVLLEYGADVNAQDKFGKTAFDISIDN<br>GNEDLAEILQKLN (SEQ ID NO: 9) |
| 2XZD | MRGSHHHHHHGSDLGKKLLEATRAGQDDEVRILMANGADVN<br>AMDDAGVTPLHLAAKRGHLEIVEVLLKHGADVNASDIWGRT<br>PLHLAATVGHLEIVEVLLEYGADVNAQDKFGKTAFDISIDN<br>GNEDLAEILQKLN (SEQ ID NO: 10) |
| 2V4H | HHHHHHHHHHGSDLGKKLLEAARAGQDDEVRILMANGADVN<br>ANDRKGNTPLHLAADYDHLEIVEVLLKHGADVNAHDNDGST<br>PLHLAALFGHLEIVEVLLKHGADVNAQDKFGKTAFDISIDN<br>GNEDLAEILQKLN (SEQ ID NO: 11) |

TABLE 2

DARPin containing 5 ANK repeats

| DARPin | Amino acid sequence |
| --- | --- |
| 2Y1L | MRGSHHHHHHGSDLGKKLLEAARAGRDDEVRILMANGADVN<br>AEDASGWTPLHLAAFNGHLEIVEVLLKNGADVNAVDHAGMT<br>PLRLAALFGHLEIVEVLLKNGADVNANDMEGHTPLHLAAMF<br>GHLEIVEVLLKNGADVNAQDKFGKTAFDISIDNGNEDLAEI<br>LQKLN (SEQ ID NO: 12) |
| 2J8S | MRGSHHHHHHGSDLGKKLLEAARAGRDDEVRILMANGADVN<br>AADVVGWTPLHLAAYVVGHLEIVEVLLKNGADVNAYDTLGS<br>TPLHLAAHFGHLEIVEVLLKNGADVNAKDDNGITPLHLAAN<br>RGHLEIVEVLLKYGADVNAQDKFGKTAFDISINNGNEDLAE<br>ILQKLN (SEQ ID NO: 13) |
| 4DX6 | MRGSHHHHHHGSDLGKKLLEAARAGRDDEVRILMANGADVN<br>AADVVGWTPLHLAAYWGHLEIVEVLLKNGADVNAYDTLGST<br>PLHLAAHFGHLEIVEVLLKNGADVNAKDDNGITPLHLAANR<br>GHLEIVEVLLKYGADVNAQDKFGKTAFDISINNGNEDLAEI<br>LQKLN (SEQ ID NO: 14) |
| 4DRX | MRGSHHHHHHGSDLGKKLLEAARAGQDDEVRILMANGADVN<br>ATDASGLTPLHLAATYGHLEIVEVLLKHGADVNAIDIMGST<br>PLHLAALIGHLEIVEVLLKHGADVNAVDTWGDTPLHLAAIM<br>GHLEIVEVLLKHGADVNAQDKFGKTAFDISIDNGNEDLAEI<br>LQKLN (SEQ ID NO: 15) |
| 2P2C | MRGSHHHHHHGSDLGKKLLEAARAGQDDEVRILMANGADVN<br>ATDWLGHTPLHLAAKTGHLEIVEVLLKYGADVNAWDNYGAT<br>PLHLAADNGHLEIVEVLLKHGADVNAKDYEGFTPLHLAAYD<br>GHLEIVEVLLKYGADVNAQDKFGKTAFDISIDNGNEDLAEI<br>LQKLN (SEQ ID NO: 16) |
| 3NOG | MRGSHHHHHHGSDLGKKLLEAARAGQDDEVRILMANGADVN<br>ASDHVGWTPLHLAAYFGHLEIVEVLLKNGADVNADDSLGVT<br>PLHLAADRGHLEVVEVLLKNGADVNANDHNGFTPLHLAANI<br>GHLEIVEVLLKHGADVNAQDKFGKTAFDISIDNGNEDLAEI<br>LQKLN (SEQ ID NO: 17) |

(In Tables 1 and 2, the underlined regions of the amino acid sequences represent an N-terminal His tag for purification, and may be omitted/removed from the final purified proteins)

Considering structural similarity, the reference protein may be a DARPin containing 4 ANK repeats (e.g., DARPin 3HGO, 2Y0B, 2XZT, 2XZD, 2V4H, etc.) when the protein of interest is p15 or p16, and a DARPin containing 5 ANK repeats (e.g., DARPin 2Y1L, 2J8S, 4DX6, 5V5Q, 4DRX, 2P2C, 3NOG, etc.) when the protein of interest is p18 or p19.

The method for providing information for a protein of interest in solubility or a method for increasing a protein of interest in solubility may be based on the method for analyzing the protein of interest for secondary or tertiary structure. The information providing method may contribute to an increase in the solubility of the protein of interest by providing information on positions at which mutations relevant to solubility might be performed.

In another embodiment, a method of providing information for increasing solubility of a protein of interest or a method of increasing solubility of a protein of interest may comprise:

comparing solvent-exposed (e.g., aqueous solvent-exposed) regions between the protein of interest and a reference protein through secondary or tertiary structure-based amino acid sequence alignment; and searching for and identifying a position (amino acid) of the solvent exposed region of the protein of interest where the protein of interest has a hydrophobic amino acid while the reference protein has a hydrophilic amino acid at the corresponding position of the solvent exposed region of the reference protein.

The protein of interest and the reference protein available for the method are as described above.

In another embodiment, the method for providing information for increasing a protein of interest in solubility or a method for increasing a protein of interest in solubility may further comprise selecting the reference protein prior to the comparison of solvent-exposed (e.g., aqueous solvent-exposed) regions between the two proteins (protein of interest/reference protein).

In addition, the method for providing information for increasing a protein of interest in solubility or a method for increasing a protein of interest in solubility may further comprise preparing information on the secondary or tertiary structures of both the protein of interest and the reference protein prior to the comparison of solvent-exposed regions between the two proteins (and/or subsequent to the selection of the reference protein). Information on the secondary or tertiary structures of proteins of interest and reference proteins may be found in various databases or obtained using a protein structure (sequence) analysis tool (such as a general device and/or software). The database and/or the analysis tool available for preparing information on the secondary or tertiary structures of proteins are well known in the art. For example, information from Phyre2 (Imperial College of London, Structural Bioinformatics Group, available online at <<http://www.sbg.bio.ic.ac.uk/phyre2/>>), and/or DALI database available online at <<ekhidna.biocenter.helsinki.fi/dali_server/>>) may be searched for, using a typical protein structure (sequence) analysis tool (e.g., ClustalW2 tool (available online at <<www.ebi.ac.uk/Tools/msa/clustalw 2/>>) for secondary alignment, Coot program (available online at <<www.ysbl.york.ac.uk/~lohkamp/coot/wincoot-download.html>>) for tertiary structure-based alignment and the like).

For use in the comparison step, the solvent-exposed regions of proteins of interest and reference proteins may be determined with reference to information on the secondary or tertiary structures of the proteins.

If an amino acid at a position of the solvent exposed region of the protein of interest is hydrophobic while an amino acid at the corresponding position of the solvent exposed region of the reference protein is hydrophilic, the hydrophobic amino acid of the protein of interest may be a candidate for mutation (substitution). Its substitution with a hydrophobic amino acid may increase the solubility of the protein of interest.

Therefore, the method of increasing solubility of the protein of interest may further comprise substituting the selected hydrophobic amino acid of the protein of interest with a hydrophilic amino acid, subsequent to the searching/identifying step. In one embodiment, the method for increasing solubility of a protein of interest comprises:

comparing solvent-exposed regions of the protein of interest and a reference protein through secondary or tertiary structure-based alignment therebetween;

searching for a position of the solvent exposed region of the protein of interest where the protein of interest has a hydrophobic amino acid while the reference protein has a hydrophilic amino acid at the corresponding position of the solvent exposed region of the reference protein; and substituting the hydrophobic amino acid at the position in the protein of interest with a hydrophilic amino acid.

The hydrophobic amino acid to be substituted may be selected from the group consisting of leucine, cysteine, valine, phenyl alanine (F), tryptophan (W), isoleucine (I), proline (P), methionine (M), and a combination thereof. As a substituent, the hydrophilic amino acid may be selected from the group consisting of lysine (K), aspartic acid (D), glutamic acid (E), glutamine (Q), asparagine (N), serine (S), alanine (A), threonine (T), and arginine (R). One or more hydrophobic amino acids may be candidates for mutation and may be independently substituted with the same or different hydrophilic amino acids. In addition, selection may be made of a hydrophobic amino acid in consideration of the size (e.g., volume and/or molecular weight) of the originally positioned hydrophobic amino acid to be substituted in order to prevent a significant change in the secondary or tertiary structure of the protein of interest or a negative effect on the original function of the protein of interest after mutation (substitution), which can be determined by a person skilled in the relevant art.

A mutation without a significant change in the secondary or tertiary structure (original function) of a wild-type protein is not difficult for a person having ordinary skill in the art.

For example, the suitable hydrophilic amino acids substitutable for each hydrophobic amino acid without substantial change in the secondary or tertiary structure of the protein of interest or a negative effect on the original function of the protein of interest, are summarized in the following table:

| Hydrophobic amino acid | Suitable hydrophilic amino acid |
|---|---|
| Leucine (L) | aspartic acid (D), arginine (R), lysine (K), glutamic acid (E), glutamine (Q), serine (S), asparagine (N), or threonine (T) |
| Cysteine (C) | serine (S) |
| Valine (V) | alanine (A), aspartic acid (D), glutamic acid (E), glutamine (Q), or asparagine (N) |
| Phenyl alanine (F) | Tyrosine (Y), Histidine (H) |
| Tryptophan (W) | lysine (K), arginine (R), aspartic acid (D), glutamic acid (E), glutamine (Q), asparagine (N), or serine (S) |
| Isoleucine (I) | aspartic acid (D), glutamic acid (E), glutamine (Q), serine (S), asparagine (N), or threonine (T) |
| Methionine (M) | aspartic acid (D), glutamic acid (E), glutamine (Q), serine (S), asparagine (N), or threonine (T) |

The mutation candidates are hydrophobic amino acids and their positions may fall within the solvent-exposed regions and not affecting to a site responsible for the inherent function of the protein, for example, an active site of the protein of interest or an interaction (binding) site between the protein of interest and its target.

As it is greatly improved in solubility, the p15 protein variant can be formulated to a stable form, with the concomitant retention of affinity for Cdk4/6. Thus, it can be usefully applied to the treatment of cancer. Given a linkage to a cell membrane penetration peptide, the p15 protein variant can be encouraged to exhibit more potent anticancer activity.

EXAMPLES

Hereafter, the present invention will be described in detail by examples.

The following examples are intended merely to illustrate the invention and are not construed to restrict the invention.

Example 1

Determination of Mutation Position of p15 Protein

The positions at which hydrophobic amino acids located with external exposure on the three dimensional structure of p15 protein were to be substituted by hydrophilic amino acids were determined in the following experiments.

With the aid of Phyre2 (<<www.sbg.bio.ic.ac.uk/phyre2/>>), the human p15 protein (SEQ ID NO: 1) was analyzed for secondary structure (see FIG. 27), and its three-dimensional structure was modeled (see FIG. 3).

A DALI database (<<ekhidna.biocenter.helsinki.fi/dali_server>>) search identified that a DARPin containing 3 ANK repeats (PDB 3HG0) (SEQ ID NO: 7) is the most similar in three dimensional structure to human p15 protein, and is expressed in *E. coli*, with an increased solubility. Based on this result, the DARPin (PDB 3HG0) (SEQ ID NO: 7) was employed as a template to determine the mutation points of the p15 protein.

The human p15 protein (SEQ ID NO: 1) and DARPin 3HG0 (SEQ ID NO: 7) was subjected to amino acid sequence alignment based on secondary structural (mainly α-helix) position, and the obtained results are shown in FIG. 4. The LSQKAB program in CCP4 module (ftp://ftp.ccp4.ac.uk/ccp4/4.0.1/ccp4-4.0.1/ccp4i/help/modules/coord_utils.html) (least-square method) was used for confirming the structural similarity between human p15 protein and DARPin 3HG0 (SEQ ID NO: 7).

Based on the basis of the secondary (mainly α-helix) or tertiary structures obtained above, leucine at position 67 (L67), cysteine at position 74 (C74), leucine at position 80 (L80), valine at position 108 (V108), and leucine at position 115 (L115), of human p15 protein (SEQ ID NO: 1), were determined as hydrophobic residues that are exposed to solvent-exposed area and have no influence on the binding with Cdk4/6, to be determined as mutation points of p15 protein.

Example 2

Preparation of Strain Expressing p15 Protein Variant

Human p15 protein (wild-type) (SEQ ID NO: 1) and a p15 protein variant (SEQ ID NO: 2) in which substitution of leucine at position 67 (L67) with lysine (K), cysteine at position 74 (C74) with serine (S), leucine at position 80 (L80) with serine (S), valine at position 108 (V108) with alanine (A), and leucine at position 115 (L115) with threonine (T) were prepared.

To prepare the human p15 protein (wild-type) of SEQ ID NO: 1 and the p15 protein variant of SEQ ID NO: 2, polynucleotides encoding them (human p15 protein: SEQ ID NO: 6; human p15 protein variant: SEQ ID NO: 3) were used. In detail, the polynucleotides were cloned to pET21b vector (Novagen) using the restriction enzymes NdeI (NEB) and XhoI (NEB) to construct recombinant vectors pET21b:WT p15INK4b, and pET21b:p15INK4b variant which were configured to express human p15 protein (wild-type) and human p15 protein variant, respectively. These recombinant vectors were introduced into an *E. coli* strain (BL21(DE3) Codon Plus-RIPL; Invitrogen) to afford recombinant strains pET21b:WT p15INK4b/BL21(DE3)CodonPlus-RIPL and pET21b:p15INK4b variant/BL21(DE3)Codon Plus-RIPL which aimed to express the human p15 protein (wild-type) and the human p15 protein variant, respectively.

Example 3

Solubility of p15 Protein Variant

Each of the recombinant strains prepared in Example 2, pET21b:WTp15INK4a/BL21(DE3)CodonPlus-RIPL (100 µL) and pET21b:p15INK4a variant/BL21(DE3)Codon Plus-RIP (100 µL) was inoculated to 5 mL of LB broth (Sigma; Tryptone (pancreatic digest of casein) 10 g/L, Yeast extract 5 g/L, NaCl 5 g/L), and incubated O/N(overnight) at 37° C. When OD600 reached ~0.8, culturing was continued at 18° C. for 12 hours in the presence of 1 mM IPTG (Isopropyl-β-D-thio-galactoside).

5 mL of the culture was centrifuged at 4° C. and 4000 rpm for 10 min. The cell pellet was resuspended in 0.4 mL of a lysis buffer (1×PBS pH 7.4), followed by sonication (pulse 1 s/1 s, 50% amplitude, 1 min) to lyse the cells. 20 µL was sampled from the cell lysate (total sample: total). After centrifugation of the cell lysate at 4° C. and 13200 rpm for 10 min, 20 µL was sampled from the supernatant (supernatant sample: sup). Separately, the inclusion body (IB) precipitate was resuspended in 0.4 mL of 1×PBS pH 7.4, and 20 µL was sampled from the suspension (inclusion body sample). Each sample was boiled at 95° C. for 5 min and then subjected to SDS-PAGE.

Figure 6:
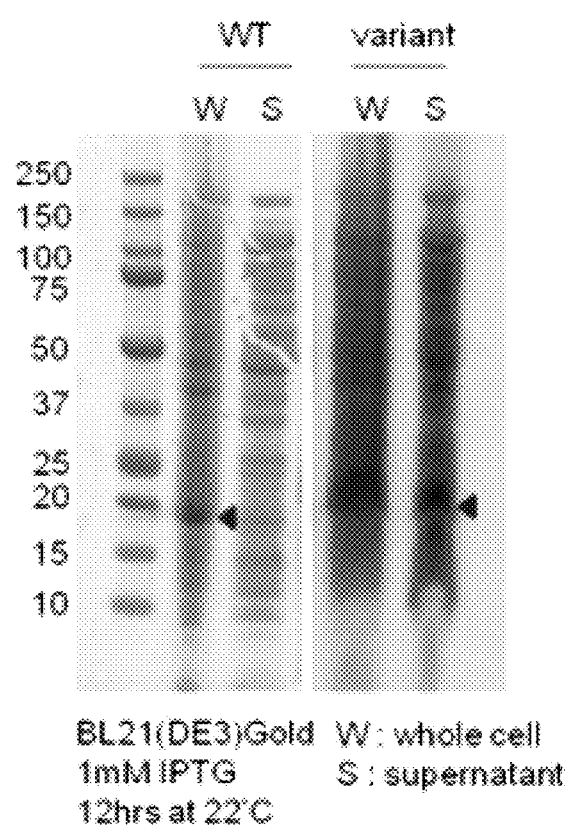
FIG. 6 is an SDS-PAGE analysis showing the protein expression profiles of wild-type p15 protein (left) and p15 protein variant (right).

The results are shown in FIG. 6. As can be seen in FIG. 6, most of the wild-type p15 protein (almost 100%) was detected in the whole cell (W), whereas most of the p15 protein variant (more than 90%) was detected in the supernatant (s). These results indicate that almost all of the wild-type p15 protein was expressed in an insoluble form in the *E. coli* strain whereas more than 90% of the p15 protein variant was expressed as a soluble entity. The soluble protein was extracellularly secreted through the cell membrane, as demonstrated by an increase in the extracellular amount of the protein (molecular weight of p15: 14721.6 Da and p15 variant: 14654.4 Da).

Example 4

Purification of p15 Protein Variant

A suspension of 2 mL of pET21b:p15INK4a variant/BL21(DE3)Codon Plus-RIPL (primary culture), prepared in Example 2, in 1 L of LB broth (Sigma; Tryptone (pancreatic digest of casein) 10 g/L, Yeast extract 5 g/L, NaCl5 g/L) was incubated O/N(overnight) at 37° C.

When OD600 reached ~0.8, 1 mM IPTG (Isopropyl-β-D-thio-galactoside) was added to the culture before incubation at 18° C. for an additional 12 hrs. The cell culture (1 L) was centrifuged at 4° C. and 4000 rpm for 10 min, and the cell pellet was resuspended in 50 mL of a lysis buffer (20 mM Tris-HCl pH8.0, 1 mM PMSF), followed by sonication (pulse 1 s/1 s, 50% amplitude, 1 min, 4 times total). After centrifugation of the resulting cell lysate at 4° C. and 18000 rpm for 50 min, the supernatant was purified by ion-exchange chromatography using an AKTA FPLC system (GE Healthcare). The following column and buffer were used:

Column. HisTrap crude FF, 5 mL size, GE Healthcare,
Buffer: A=20 mM Tris-HCl pH7.4, 200 mM NaCl, B=20 mM Tris-HCl pH7.4, 200 mM NaCl, 500 mM imidazole.

The p15 protein variant was eluted using a linear gradient (0→500 mM imidazole, 100 mL length). The eluate was subjected to size-exclusion chromatography (SEC) using the following column and buffer:

Column: 10/300 superdex-75 gl (GE Healthcare)
Buffer: 1×PBS pH 7.4

The p15 protein variant fraction obtained by SEC was purified to a final concentration of 5 mg/mL (3 mM) by ultrafiltration using YM-10 filter (Millipore).

Figure 7:
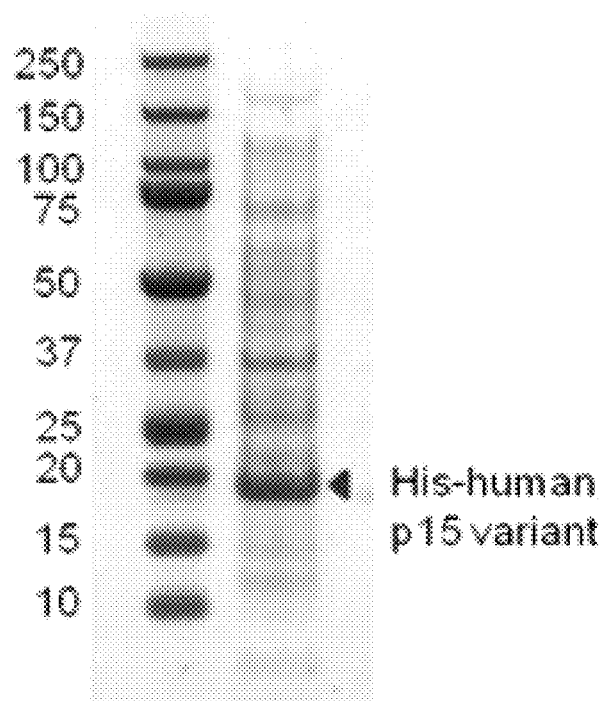
FIG. 7 is an SDS-PAGE analysis showing the amount of human p15 protein variant which is eluted from His-affinity column.

The purification result is illustrated in FIG. 7. As shown in FIG. 7, the purified p15 protein variant was homogeneous in size as measured by size-exclusion chromatography, and could be concentrated to more than 0.3 mM.

Example 5

Assay for Binding of p15 Protein Variant to Cdk4/6

The binding affinity of p15 protein variant prepared in Example 2 and Cdk4/6 was examined as follows:

A Cdk6 (Abcam's ab84717, recombinant full length Human Cdk6 (amino acids 1-326) with N-terminal His tag) was diluted to 1 μg/ml in a bicarbonate/carbonate buffer (100 mM, pH 9.6; 3.03 g Na$_2$CO$_3$, 6.0 g NaHCO$_3$, in 1000 ml distilled water), and 50 μL of the dilution was aliquoted to each well of 96-well plates (Nun's MaxiSorp) for ELISA and incubated overnight at 4° C. After aspiration of the Cdk6 solution therefrom, each well of the plates was washed twice with 200 μL of PBST (PBS+Tween 20: 1.16 g Na$_2$HPO$_4$, 0.1 g KCl, 0.1 g K$_3$PO$_4$, 4.0 g NaCl (in 500 ml distilled water), pH 7.4; 0.05% (v/v) Tween 20). Then, each well thus coated with Cdk6 was incubated with 200 μL of a blocking solution (5% (v/v) skim milk in PBST) at room temperature for 1 hr, followed by two rounds of washing with PBST 200 μL of PBST.

To each well coated with the Cdk6 protein, 100 μL of the p15 protein variant purified at various concentrations (0, 0.001, 0.01, 0.1, 1, and 10 μM) in Example 3 was added. After 2 hours of incubation at room temperature, unreacted proteins were removed, and each well was washed twice with 200 μL of PBST.

Each well was added with 100 μL of a 1/200 dilution of anti-GST antibody (GE Healthcare's; 17-4577-01 primary) in a blocking solution (5%(v/v) skim milk in PBST) and incubated at room temperature for 1 hr. After removal of the antibody solution, each well was washed twice with 200 μL of PBST.

A 1/10000 dilution of anti-goat IgG antibody (HRP) (Thermo's PA1-28664; secondary antibody) in a blocking solution was added in an amount of 100 μL to each well, and incubated at room temperature for 30 min. Thereafter, after removal of the antibody solution, each well washed four times with 200 μL of PBST and then twice with 200 μL of PBS.

After complete removal of the washing solution, 100 μL of Super AquaBlue ELISA Substrate solution (eBioscience, Cat.Number: #00-4203-58), as a chromogenic substrate, was added to each well. When a color developed to the desired intensity, the absorbance at 450 nm was read on a microwell reader (Molecular Device, Model: 340PC384). For comparison, p16 protein (wild-type; SEQ ID NO: 18) and p16 protein variant (SEQ ID NO: 19) which have structural similarity with p15 protein of SEQ ID NO: 1 (wild-type) were assayed for binding to Cdk6 in the same manner.

Figure 8:
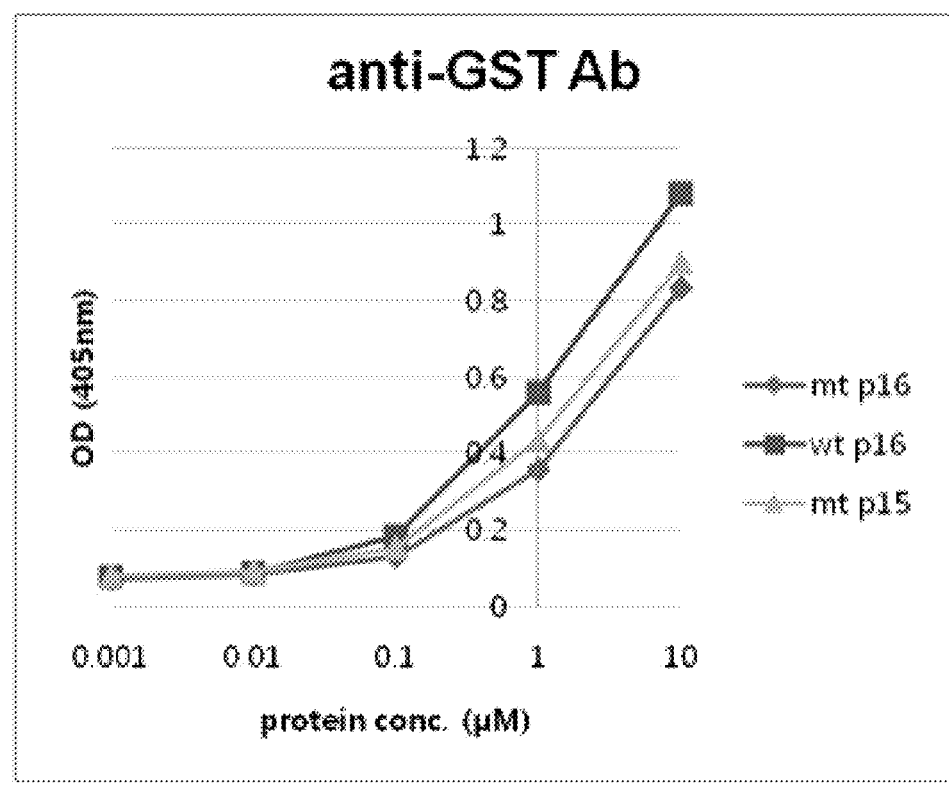
FIG. 8 is a graph showing the binding affinity of p15 protein variant to Cdk6 protein as compared to human p16 protein and a p16 protein variant.

Results are given in FIG. 8 (mt p15: p15 protein variant; wt p16: wild-type p16 protein; and mt p16: p16 protein variant). As apparent from the data of FIG. 8, the p15 protein variant (mt p15) prepared in Example 2 retained affinity for the Cdk6 protein to the same degree as the wild-type p16 protein (wt p16), which has structural similarity with wild-type p15 protein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant or synthetic p15 protein variant comprising a p15 protein in which at least one hydrophobic amino acid residue that is externally exposed on the tertiary structure of the p15 protein in aqueous solution is substituted with a hydrophilic amino acid, wherein the hydrophobic amino acid is leucine (L), cysteine (C), valine (V), phenyl alanine (F), tryptophan (W), isoleucine (I), proline (P), methionine (M), or a combination thereof; and the hydrophilic amino acid is lysine (K), aspartic acid (D), glutamic acid (E), glutamine (Q), asparagine (N), serine (S), alanine (A), threonine (T), arginine (R), or a combination thereof.

2. The recombinant or synthetic p15 protein variant of claim 1, wherein the p15 protein variant comprises a polypeptide of SEQ ID NO: 22, wherein at least one of X$_1$, X$_2$, X$_3$, X$_6$, and X$_8$ is independently selected from hydrophilic amino acids comprising serine (S), lysine (K), aspartic acid (D), glutamic acid (E), glutamine (Q), asparagine (N), alanine (A), threonine (T), and arginine (R).

3. The recombinant or synthetic p15 protein variant of claim 1, wherein
the p15 protein variant comprises SEQ ID NO: 1 in which at least one of leucine at position 67 (L67), cysteine at position 74 (C74), leucine at position 80 (L80), valine at position 108 (V108) and leucine at position 115 (L115), of SEQ ID NO: 1, is independently substituted with lysine (K), aspartic acid (D), glutamic acid (E), glutamine (Q), asparagine (N), serine (S), alanine (A), threonine (T), or arginine (R).

4. The recombinant or synthetic p15 protein variant of claim 3, wherein the p15 protein variant comprises SEQ ID NO: 1 having at least one substitution selected from the group consisting of:
  a substitution of leucine at position 67 (L67) of SEQ ID NO: 1 with lysine (K), arginine (R), aspartic acid (D), glutamic acid (E), glutamine (Q), asparagine (N), or serine (S),
  a substitution of cysteine at position 74 (C74) of SEQ ID NO: 1 with serine (S),
  a substitution of leucine at position 80 (L80) of SEQ ID NO: 1 with serine (S), arginine (R), lysine (K), aspartic acid (D), glutamic acid (E), glutamine (Q), or asparagine (N),
  a substitution of valine at position 108 (V108) of SEQ ID NO: 1 with alanine (A), aspartic acid (D), glutamic acid (E), glutamine (Q), or asparagine (N), and
  a substitution of leucine at position 115 (L115) of SEQ ID NO: 1 with threonine (T), arginine (R), lysine (K), aspartic acid (D), glutamic acid (E), glutamine (Q), asparagine (N), or serine (S).

5. The recombinant or synthetic p15 protein variant of claim 1, wherein the p15 protein variant comprises SEQ ID NO: 2.

6. The recombinant or synthetic p15 protein variant of claim 1, wherein
the p15 protein variant comprises the amino acid sequence of SEQ ID NO: 4 or SEQ ID NO: 5, in which at least one selected from the group consisting of leucine at positions 59 (L59), cysteine at position 66 (C66), leucine at position 72 (L72), valine at position 100 (V100), and leucine at position 107 (L107), of SEQ ID NO: 4 or SEQ ID NO: 5, is independently substituted with lysine (K), aspartic acid (D), glutamic acid (E), glutamine (Q), asparagine (N), serine (S), alanine (A), threonine (T), or arginine (R).

7. The recombinant or synthetic p15 protein variant of claim 1, wherein
the p15 protein variant comprises the amino acid sequence of SEQ ID NO: 4 or SEQ ID NO: 5 comprising at least one selected from the group consisting of:
a substitution of leucine at position 59 (L59) on the amino acid sequence of SEQ ID NO: 4 or SEQ ID NO: 5 with lysine (K), arginine (R), aspartic acid (D), glutamic acid (E), glutamine (Q), asparagine (N), or serine (S),
a substitution of cysteine at position 66 (C66) on the amino acid sequence of SEQ ID NO: 4 or SEQ ID NO: 5 with serine (S),
a substitution of leucine at position 72 (L72) on the amino acid sequence of SEQ ID NO: 4 or SEQ ID NO: 5 with serine (S), arginine (R), lysine (K), aspartic acid (D), glutamic acid (E), glutamine (Q), or asparagine (N),
a substitution of valine at position 100 (V100) on the amino acid sequence of SEQ ID NO: 4 or SEQ ID NO: 5 with alanine (A), aspartic acid (D), glutamic acid (E), glutamine (Q), or asparagine (N), and
a substitution of leucine at position 107 (L107) on the amino acid sequence of SEQ ID NO: 4 or SEQ ID NO: 5 with threonine (T), arginine (R), lysine (K), aspartic acid (D), glutamic acid (E), glutamine (Q), asparagine (N), or serine (S).

8. A polynucleotide encoding the recombinant or synthetic p15 protein variant of claim 1.

9. The polynucleotide of claim 8 comprising the nucleotide sequence of SEQ ID NO: 3.

10. A recombinant vector comprising the polynucleotide of claim 8.

11. A recombinant cell comprising the recombinant vector of claim 10.

12. A pharmaceutical composition comprising the recombinant or synthetic p15 protein variant of claim 1 and a carrier.

13. A method of preventing or treating cancer in a subject, comprising administering the recombinant or synthetic p15 protein variant of claim 1 to the subject.

14. The method of claim 13, wherein the recombinant or synthetic p15 protein variant comprises the amino acid sequence of SEQ ID NO: 2.

15. A method of providing a recombinant or synthetic p15 protein variant having increased solubility, comprising substituting at least one hydrophobic amino acid residue that is externally exposed on the tertiary structure of a p15 protein, independently with a hydrophilic amino acid,
wherein the hydrophobic amino acid is leucine (L), cysteine (C), valine (V), phenyl alanine (F), tryptophan (W), isoleucine (I), proline (P), methionine (M), or a combination thereof; and the hydrophilic amino acid is lysine (K), aspartic acid (D), glutamic acid (E), glutamine (Q), asparagine (N), serine (S), alanine (A), threonine (T), arginine (R), or a combination thereof.

16. The method of claim 15, wherein the hydrophobic amino acid residues that are externally exposed on the tertiary structure of p15 protein and suitable for substitution with a hydrophilic amino acid are identified by structural comparison of the p15 protein with a designed ankyrin repeat protein (DARPin) comprising 4 or 5 ankyrin (ANK) repeat motifs.

17. The method of claim 15, wherein the step of substituting is performed by preparing a polypeptide comprising SEQ ID NO: 1 in which at least one of leucine at position 67 (L67), cysteine at position 74 (C74), leucine at position 80 (L80), valine at position 108 (V108) and leucine at position 115 (L115), of SEQ ID NO: 1, independently with lysine (K), aspartic acid (D), glutamic acid (E), glutamine (Q), asparagine (N), serine (S), alanine (A), threonine (T), or arginine (R).

18. The method of claim 15, wherein the step of substituting is performed by preparing a polypeptide comprising SEQ ID NO: 4 or SEQ ID NO: 5 in which at least one of leucine at positions 59 (L59), cysteine at position 66 (C66), leucine at position 72 (L72), valine at position 100 (V100), and leucine at position 107 (L107), of SEQ ID NO: 4 or SEQ ID NO: 5, independently with lysine (K), aspartic acid (D), glutamic acid (E), glutamine (Q), asparagine (N), serine (S), alanine (A), threonine (T), or arginine (R).

19. The method of claim 16, wherein the DARPin is at least one selected from the group consisting of DARPin 3HGO, DARPin 2Y0B, DARPin 2XZT, DARPin 2XZD, DARPin 2V4H, DARPin 2Y1L, DARPin MS, DARPin 4DX6, DARPin 5V5Q, DARPin 4DRX, DARPin 2P2C, and DARPin 3NOG.

20. The method of claim 17, wherein the polypeptide is prepared by expressing a polynucleotide encoding the polypeptide in a cell.

* * * * *

SEQUENCE LISTING

<160> NUMBER OF SEQ ID NOS: 22

<210> SEQ ID NO 1
<211> LENGTH: 138
<212> TYPE: PRT
<213> ORGANISM: Artificial Sequence
<220> FEATURE:
<223> OTHER INFORMATION: Synthetic Amino Acid Sequence of Wild-Type Human p15 (Accession No. P42772)

<400> SEQUENCE: 1

```
Met Arg Glu Glu Asn Lys Gly Met Pro Ser Gly Gly Ser Asp Glu
  1               5                  10                  15

Gly Leu Ala Ser Ala Ala Arg Gly Leu Val Glu Lys Val Arg Gln
                 20                  25                  30

Leu Leu Glu Ala Gly Ala Asp Pro Asn Gly Val Asn Arg Phe Gly Arg
             35                  40                  45

Arg Ala Ile Gln Val Met Met Met Gly Ser Ala Arg Val Ala Glu Leu
         50                  55                  60

Leu Leu Leu His Gly Ala Glu Pro Asn Cys Ala Asp Pro Ala Thr Leu
 65                  70                  75                  80

Thr Arg Pro Val His Asp Ala Ala Arg Glu Gly Phe Leu Asp Thr Leu
                     85                  90                  95

Val Val Leu His Arg Ala Gly Ala Arg Leu Asp Val Arg Asp Ala Trp
                100                 105                 110

Gly Arg Leu Pro Val Asp Leu Ala Glu Glu Arg Gly His Arg Asp Val
            115                 120                 125

Ala Gly Tyr Leu Arg Thr Ala Thr Gly Asp
        130                 135
```

<210> SEQ ID NO 2
<211> LENGTH: 138
<212> TYPE: PRT
<213> ORGANISM: Artificial Sequence
<220> FEATURE:
<223> OTHER INFORMATION: Synthetic Amino Acid Sequence of Human p15 Variant

<400> SEQUENCE: 2

```
Met Arg Glu Glu Asn Lys Gly Met Pro Ser Gly Gly Ser Asp Glu
  1               5                  10                  15

Gly Leu Ala Ser Ala Ala Arg Gly Leu Val Glu Lys Val Arg Gln
                 20                  25                  30

Leu Leu Glu Ala Gly Ala Asp Pro Asn Gly Val Asn Arg Phe Gly Arg
             35                  40                  45

Arg Ala Ile Gln Val Met Met Met Gly Ser Ala Arg Val Ala Glu Leu
         50                  55                  60

Leu Leu Lys His Gly Ala Glu Pro Asn Ser Ala Asp Pro Ala Thr Ser
 65                  70                  75                  80

Thr Arg Pro Val His Asp Ala Ala Arg Glu Gly Phe Leu Asp Thr Leu
                     85                  90                  95

Val Val Leu His Arg Ala Gly Ala Arg Leu Asp Ala Arg Asp Ala Trp
                100                 105                 110

Gly Arg Thr Pro Val Asp Leu Ala Glu Glu Arg Gly His Arg Asp Val
            115                 120                 125

Ala Gly Tyr Leu Arg Thr Ala Thr Gly Asp
        130                 135
```

<210> SEQ ID NO 3
<211> LENGTH: 417
<212> TYPE: DNA
<213> ORGANISM: Artificial Sequence
<220> FEATURE:
<223> OTHER INFORMATION: Synthetic DNA Sequence of human p15 variant

<400> SEQUENCE: 3

```
atgcgcgaag aaaacaaagg catgccgagc ggcggcggca gcgatgaagg cctggcgagc      60
gcggcggcgc gcggcctggt ggaaaaagtg cgccagctgc tggaagcggg cgcggatccg     120
aacggcgtga accgctttgg ccgccgcgcg attcaggtga tgatgatggg cagcgcgcgc     180
gtggcggaac tgctgctgaa acatggcgcg gaaccgaaca gcgcggatcc ggcgaccagc     240
acccgcccgg tgcatgatgc ggcgcgcgaa ggctttctgg ataccctggt ggtgctgcat     300
cgcgcgggcg cgcgcctgga tgcgcgcgat cgtgggggcc gcaccccggt ggatctggcg     360
gaagaacgcg gccatcgcga tgtggcgggc tatctgcgca ccgcgaccgg cgattaa       417
```

<210> SEQ ID NO 4
<211> LENGTH: 130
<212> TYPE: PRT
<213> ORGANISM: Artificial Sequence
<220> FEATURE:
<223> OTHER INFORMATION: Synthetic Mouse p15-INK4b; P55271

<400> SEQUENCE: 4

```
Met Leu Gly Gly Ser Ser Asp Ala Gly Leu Ala Thr Ala Ala Ala Arg
  1               5                  10                  15
Gly Gln Val Glu Thr Val Arg Gln Leu Leu Glu Ala Gly Ala Asp Pro
             20                  25                  30
Asn Ala Leu Asn Arg Phe Gly Arg Arg Pro Ile Gln Val Met Met Met
         35                  40                  45
Gly Ser Ala Gln Val Ala Glu Leu Leu Leu Leu His Gly Ala Glu Pro
     50                  55                  60
Asn Cys Ala Asp Pro Ala Thr Leu Thr Arg Pro Val His Asp Ala Ala
 65                  70                  75                  80
Arg Glu Gly Phe Leu Asp Thr Leu Val Val Leu His Arg Ala Gly Ala
                 85                  90                  95
Arg Leu Asp Val Cys Asp Ala Trp Gly Arg Leu Pro Val Asp Leu Ala
            100                 105                 110
Glu Glu Gln Gly His Arg Asp Ile Ala Arg Tyr Leu His Ala Ala Thr
        115                 120                 125
Gly Asp
    130
```

<210> SEQ ID NO 5
<211> LENGTH: 130
<212> TYPE: PRT
<213> ORGANISM: Artificial Sequence
<220> FEATURE:
<223> OTHER INFORMATION: Synthetic Rat p15-INK4b; P55272

<400> SEQUENCE: 5

```
Met Leu Gly Gly Gly Ser Asp Ala Gly Leu Ala Thr Ala Ala Ala Arg
  1               5                  10                  15
Gly Gln Val Glu Thr Val Arg Gln Leu Leu Glu Ala Gly Ala Asp Pro
             20                  25                  30
Asn Ala Val Asn Arg Phe Gly Arg Arg Pro Ile Gln Val Met Met Met
         35                  40                  45
```

```
Gly Ser Ala Gln Val Ala Glu Leu Leu Leu His Gly Ala Glu Pro
        50                  55                  60

Asn Cys Ala Asp Pro Ala Thr Leu Thr Arg Pro Val His Asp Ala Ala
 65                  70                  75                  80

Arg Glu Gly Phe Leu Asp Thr Leu Met Val Leu His Lys Ala Gly Ala
                 85                  90                  95

Arg Leu Asp Val Cys Asp Ala Trp Gly Arg Leu Pro Val Asp Leu Ala
                100                 105                 110

Glu Glu Gln Gly His Arg Asp Ile Ala Arg Tyr Leu His Ala Ala Thr
            115                 120                 125

Gly Asp
    130

<210> SEQ ID NO 6
<211> LENGTH: 417
<212> TYPE: DNA
<213> ORGANISM: Artificial Sequence
<220> FEATURE:
<223> OTHER INFORMATION: Synthetic DNA sequence of wild-type human p15
      protein

<400> SEQUENCE: 6
atgcgcgaag aaacaaagg catgccgagc ggcggcggca gcgatgaagg cctggcgagc      60
gcggcggcgc gcggcctggt ggaaaaagtg cgccagctgc tggaagcggg cgcggatccg    120
aacggcgtga accgctttgg ccgccgcgcg attcaggtga tgatgatggg cagcgcgcgc    180
gtggcggaac tgctgctgct gcatggcgcg gaaccgaact gcgcggatcc ggcgaccctg    240
acccgcccgg tgcatgatgc ggcgcgcgaa ggctttctgg ataccctggt ggtgctgcat    300
cgcgcgggcg cgcgcctgga tgtgcgcgat gcgtggggcc gcctgccggt ggatctggcg    360
gaagaacgcg gccatcgcga tgtggcgggc tatctgcgca ccgcgaccgg cgattaa      417

<210> SEQ ID NO 7
<211> LENGTH: 136
<212> TYPE: PRT
<213> ORGANISM: Artificial Sequence
<220> FEATURE:
<223> OTHER INFORMATION: Synthetic 4 ANK repeat DARPin 3HG0
<220> FEATURE:
<221> NAME/KEY: PEPTIDE
<222> LOCATION: (1)..(10)
<223> OTHER INFORMATION: N-terminal His tag for purification

<400> SEQUENCE: 7

Met Arg Gly Ser His His His His His His Gly Ser Asp Leu Gly Lys
  1               5                  10                  15

Lys Leu Leu Glu Ala Ala Arg Ala Gly Gln Asp Asp Glu Val Arg Ile
             20                  25                  30

Leu Met Ala Asn Gly Ala Asp Val Asn Ala Glu Asp Lys Val Gly Leu
         35                  40                  45

Thr Pro Leu His Leu Ala Ala Met Asn Asp His Leu Glu Ile Val Glu
     50                  55                  60

Val Leu Leu Lys Asn Gly Ala Asp Val Asn Ala Ile Asp Ala Ile Gly
 65                  70                  75                  80

Glu Thr Pro Leu His Leu Val Ala Met Tyr Gly His Leu Glu Ile Val
                 85                  90                  95

Glu Val Leu Leu Lys His Gly Ala Asp Val Asn Ala Gln Asp Lys Phe
                100                 105                 110
```

Gly Lys Thr Ala Phe Asp Ile Ser Ile Asp Asn Gly Asn Glu Asp Leu
            115                 120                 125

Ala Glu Ile Leu Gln Lys Leu Asn
        130                 135

<210> SEQ ID NO 8
<211> LENGTH: 136
<212> TYPE: PRT
<213> ORGANISM: Artificial Sequence
<220> FEATURE:
<223> OTHER INFORMATION: Synthetic 4 ANK repeat DARPin 2Y0B
<220> FEATURE:
<221> NAME/KEY: PEPTIDE
<222> LOCATION: (1)..(10)
<223> OTHER INFORMATION: N-terminal His tag for purification

<400> SEQUENCE: 8

Met Arg Gly Ser His His His His His Gly Ser Asp Leu Gly Lys
1               5                   10                  15

Lys Leu Leu Glu Ala Thr Arg Ala Gly Gln Asp Asp Glu Val Arg Ile
            20                  25                  30

Leu Met Ala Asn Gly Ala Asp Val Asn Ala Met Asp Asp Ala Gly Val
        35                  40                  45

Thr Pro Leu His Leu Ala Ala Lys Arg Gly His Leu Glu Ile Val Glu
    50                  55                  60

Val Leu Leu Lys His Gly Ala Asp Val Asn Ala Arg Asp Ile Trp Gly
65                  70                  75                  80

Arg Thr Pro Leu His Leu Ala Ala Thr Val Gly His Leu Glu Ile Val
                85                  90                  95

Glu Val Leu Leu Glu Tyr Gly Ala Asp Val Asn Ala Gln Asp Lys Phe
            100                 105                 110

Gly Lys Thr Ala Phe Asp Ile Ser Ile Asp Asn Gly Asn Glu Asp Leu
        115                 120                 125

Ala Glu Ile Leu Gln Lys Leu Asn
    130                 135

<210> SEQ ID NO 9
<211> LENGTH: 136
<212> TYPE: PRT
<213> ORGANISM: Artificial Sequence
<220> FEATURE:
<223> OTHER INFORMATION: Synthetic 4 ANK repeat DARPin 2XZT
<220> FEATURE:
<221> NAME/KEY: PEPTIDE
<222> LOCATION: (1)..(10)
<223> OTHER INFORMATION: N-terminal His tag for purification

<400> SEQUENCE: 9

Met Arg Gly Ser His His His His His Gly Ser Asp Leu Gly Lys
1               5                   10                  15

Lys Leu Leu Glu Ala Thr Arg Ala Gly Gln Asp Asp Glu Val Arg Ile
            20                  25                  30

Leu Met Ala Asn Gly Ala Asp Val Asn Ala Met Asp Asp Ala Gly Val
        35                  40                  45

Thr Pro Leu His Leu Ala Ala Lys Arg Gly His Leu Glu Ile Val Glu
    50                  55                  60

Val Leu Leu Lys His Gly Ala Asp Val Asn Ala Ser Asp Ser Trp Gly
65                  70                  75                  80

Arg Thr Pro Leu His Leu Ala Ala Thr Val Gly His Leu Glu Ile Val
                85                  90                  95

```
Glu Val Leu Leu Glu Tyr Gly Ala Asp Val Asn Ala Gln Asp Lys Phe
                100                 105                 110

Gly Lys Thr Ala Phe Asp Ile Ser Ile Asp Asn Gly Asn Glu Asp Leu
            115                 120                 125

Ala Glu Ile Leu Gln Lys Leu Asn
        130                 135
```

<210> SEQ ID NO 10
<211> LENGTH: 136
<212> TYPE: PRT
<213> ORGANISM: Artificial Sequence
<220> FEATURE:
<223> OTHER INFORMATION: Synthetic 4 ANK repeat DARPin 2XZD
<220> FEATURE:
<221> NAME/KEY: PEPTIDE
<222> LOCATION: (1)..(10)
<223> OTHER INFORMATION: N-terminal His tag for purification

<400> SEQUENCE: 10

```
Met Arg Gly Ser His His His His His His Gly Ser Asp Leu Gly Lys
  1               5                  10                  15

Lys Leu Leu Glu Ala Thr Arg Ala Gly Gln Asp Asp Glu Val Arg Ile
             20                  25                  30

Leu Met Ala Asn Gly Ala Asp Val Asn Ala Met Asp Asp Ala Gly Val
         35                  40                  45

Thr Pro Leu His Leu Ala Ala Lys Arg Gly His Leu Glu Ile Val Glu
     50                  55                  60

Val Leu Leu Lys His Gly Ala Asp Val Asn Ala Ser Asp Ile Trp Gly
 65                  70                  75                  80

Arg Thr Pro Leu His Leu Ala Ala Thr Val Gly His Leu Glu Ile Val
                 85                  90                  95

Glu Val Leu Leu Glu Tyr Gly Ala Asp Val Asn Ala Gln Asp Lys Phe
                100                 105                 110

Gly Lys Thr Ala Phe Asp Ile Ser Ile Asp Asn Gly Asn Glu Asp Leu
            115                 120                 125

Ala Glu Ile Leu Gln Lys Leu Asn
        130                 135
```

<210> SEQ ID NO 11
<211> LENGTH: 136
<212> TYPE: PRT
<213> ORGANISM: Artificial Sequence
<220> FEATURE:
<223> OTHER INFORMATION: Synthetic 4 ANK repeat DARPin 2V4H
<220> FEATURE:
<221> NAME/KEY: PEPTIDE
<222> LOCATION: (1)..(10)
<223> OTHER INFORMATION: N-terminal His tag for purification

<400> SEQUENCE: 11

```
His His His His His His His His His His Gly Ser Asp Leu Gly Lys
  1               5                  10                  15

Lys Leu Leu Glu Ala Ala Arg Ala Gly Gln Asp Asp Glu Val Arg Ile
             20                  25                  30

Leu Met Ala Asn Gly Ala Asp Val Asn Ala Asn Asp Arg Lys Gly Asn
         35                  40                  45

Thr Pro Leu His Leu Ala Ala Asp Tyr Asp His Leu Glu Ile Val Glu
     50                  55                  60

Val Leu Leu Lys His Gly Ala Asp Val Asn Ala His Asp Asn Asp Gly
 65                  70                  75                  80
```

Ser Thr Pro Leu His Leu Ala Ala Leu Phe Gly His Leu Glu Ile Val
            85                  90                  95

Glu Val Leu Leu Lys His Gly Ala Asp Val Asn Ala Gln Asp Lys Phe
                100                 105                 110

Gly Lys Thr Ala Phe Asp Ile Ser Ile Asp Asn Gly Asn Glu Asp Leu
        115                 120                 125

Ala Glu Ile Leu Gln Lys Leu Asn
    130                 135

<210> SEQ ID NO 12
<211> LENGTH: 169
<212> TYPE: PRT
<213> ORGANISM: Artificial Sequence
<220> FEATURE:
<223> OTHER INFORMATION: Synthetic 5 ANK repeat DARPin 2Y1L
<220> FEATURE:
<221> NAME/KEY: PEPTIDE
<222> LOCATION: (1)..(10)
<223> OTHER INFORMATION: N-terminal His tag for purification

<400> SEQUENCE: 12

Met Arg Gly Ser His His His His His His Gly Ser Asp Leu Gly Lys
 1               5                  10                  15

Lys Leu Leu Glu Ala Ala Arg Ala Gly Arg Asp Asp Glu Val Arg Ile
                20                  25                  30

Leu Met Ala Asn Gly Ala Asp Val Asn Ala Glu Asp Ala Ser Gly Trp
        35                  40                  45

Thr Pro Leu His Leu Ala Ala Phe Asn Gly His Leu Glu Ile Val Glu
    50                  55                  60

Val Leu Leu Lys Asn Gly Ala Asp Val Asn Ala Val Asp His Ala Gly
65                  70                  75                  80

Met Thr Pro Leu Arg Leu Ala Ala Leu Phe Gly His Leu Glu Ile Val
                85                  90                  95

Glu Val Leu Leu Lys Asn Gly Ala Asp Val Asn Ala Asn Asp Met Glu
                100                 105                 110

Gly His Thr Pro Leu His Leu Ala Ala Met Phe Gly His Leu Glu Ile
        115                 120                 125

Val Glu Val Leu Leu Lys Asn Gly Ala Asp Val Asn Ala Gln Asp Lys
    130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Asn
                165

<210> SEQ ID NO 13
<211> LENGTH: 169
<212> TYPE: PRT
<213> ORGANISM: Artificial Sequence
<220> FEATURE:
<223> OTHER INFORMATION: Synthetic 5 ANK repeat DARPin 2J8S
<220> FEATURE:
<221> NAME/KEY: PEPTIDE
<222> LOCATION: (1)..(10)
<223> OTHER INFORMATION: N-terminal His tag for purification

<400> SEQUENCE: 13

Met Arg Gly Ser His His His His His His Gly Ser Asp Leu Gly Lys
 1               5                  10                  15

Lys Leu Leu Glu Ala Ala Arg Ala Gly Arg Asp Asp Glu Val Arg Ile
                20                  25                  30

```
Leu Met Ala Asn Gly Ala Asp Val Asn Ala Asp Val Val Gly Trp
        35                  40                  45

Thr Pro Leu His Leu Ala Ala Tyr Trp Gly His Leu Glu Ile Val Glu
    50                  55                  60

Val Leu Leu Lys Asn Gly Ala Asp Val Asn Ala Tyr Asp Thr Leu Gly
65                  70                  75                  80

Ser Thr Pro Leu His Leu Ala Ala His Phe Gly His Leu Glu Ile Val
                85                  90                  95

Glu Val Leu Leu Lys Asn Gly Ala Asp Val Asn Ala Lys Asp Asp Asn
                100                 105                 110

Gly Ile Thr Pro Leu His Leu Ala Ala Asn Arg Gly His Leu Glu Ile
            115                 120                 125

Val Glu Val Leu Leu Lys Tyr Gly Ala Asp Val Asn Ala Gln Asp Lys
            130                 135                 140

Phe Gly Lys Thr Ala Phe Asp Ile Ser Ile Asn Asn Gly Asn Glu Asp
145                 150                 155                 160

Leu Ala Glu Ile Leu Gln Lys Leu Asn
                165

<210> SEQ ID NO 14
<211> LENGTH: 169
<212> TYPE: PRT
<213> ORGANISM: Artificial Sequence
<220> FEATURE:
<223> OTHER INFORMATION: Synthetic 5 ANK repeat DARPin 4DX6
<220> FEATURE:
<221> NAME/KEY: PEPTIDE
<222> LOCATION: (1)..(10)
<223> OTHER INFORMATION: N-terminal His tag for purification

<400> SEQUENCE: 14

Met Arg Gly Ser His His His His His Gly Ser Asp Leu Gly Lys
1               5                   10                  15

Lys Leu Leu Glu Ala Ala Arg Ala Gly Arg Asp Asp Glu Val Arg Ile
                20                  25                  30

Leu Met Ala Asn Gly Ala Asp Val Asn Ala Asp Val Val Gly Trp
        35                  40                  45

Thr Pro Leu His Leu Ala Ala Tyr Trp Gly His Leu Glu Ile Val Glu
    50                  55                  60

Val Leu Leu Lys Asn Gly Ala Asp Val Asn Ala Tyr Asp Thr Leu Gly
65                  70                  75                  80

Ser Thr Pro Leu His Leu Ala Ala His Phe Gly His Leu Glu Ile Val
                85                  90                  95

Glu Val Leu Leu Lys Asn Gly Ala Asp Val Asn Ala Lys Asp Asp Asn
                100                 105                 110

Gly Ile Thr Pro Leu His Leu Ala Ala Asn Arg Gly His Leu Glu Ile
            115                 120                 125

Val Glu Val Leu Leu Lys Tyr Gly Ala Asp Val Asn Ala Gln Asp Lys
            130                 135                 140

Phe Gly Lys Thr Ala Phe Asp Ile Ser Ile Asn Asn Gly Asn Glu Asp
145                 150                 155                 160

Leu Ala Glu Ile Leu Gln Lys Leu Asn
                165

<210> SEQ ID NO 15
<211> LENGTH: 169
<212> TYPE: PRT
```

<213> ORGANISM: Artificial Sequence
<220> FEATURE:
<223> OTHER INFORMATION: Synthetic 5 ANK repeat DARPin 4DRX
<220> FEATURE:
<221> NAME/KEY: PEPTIDE
<222> LOCATION: (1)..(10)
<223> OTHER INFORMATION: N-terminal His tag for purification

<400> SEQUENCE: 15

```
Met Arg Gly Ser His His His His His Gly Ser Asp Leu Gly Lys
  1               5                  10                  15

Lys Leu Leu Glu Ala Ala Arg Ala Gly Gln Asp Asp Glu Val Arg Ile
             20                  25                  30

Leu Met Ala Asn Gly Ala Asp Val Asn Ala Thr Asp Ala Ser Gly Leu
             35                  40                  45

Thr Pro Leu His Leu Ala Ala Thr Tyr Gly His Leu Glu Ile Val Glu
         50                  55                  60

Val Leu Leu Lys His Gly Ala Asp Val Asn Ala Ile Asp Ile Met Gly
 65                  70                  75                  80

Ser Thr Pro Leu His Leu Ala Ala Leu Ile Gly His Leu Glu Ile Val
                 85                  90                  95

Glu Val Leu Leu Lys His Gly Ala Asp Val Asn Ala Val Asp Thr Trp
                100                 105                 110

Gly Asp Thr Pro Leu His Leu Ala Ala Ile Met Gly His Leu Glu Ile
             115                 120                 125

Val Glu Val Leu Leu Lys His Gly Ala Asp Val Asn Ala Gln Asp Lys
 130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Asn
                165
```

<210> SEQ ID NO 16
<211> LENGTH: 169
<212> TYPE: PRT
<213> ORGANISM: Artificial Sequence
<220> FEATURE:
<223> OTHER INFORMATION: Synthetic 5 ANK repeat DARPin 2P2C
<220> FEATURE:
<221> NAME/KEY: PEPTIDE
<222> LOCATION: (1)..(10)
<223> OTHER INFORMATION: N-terminal His tag for purification

<400> SEQUENCE: 16

```
Met Arg Gly Ser His His His His His Gly Ser Asp Leu Gly Lys
  1               5                  10                  15

Lys Leu Leu Glu Ala Ala Arg Ala Gly Gln Asp Asp Glu Val Arg Ile
             20                  25                  30

Leu Met Ala Asn Gly Ala Asp Val Asn Ala Thr Asp Trp Leu Gly His
             35                  40                  45

Thr Pro Leu His Leu Ala Ala Lys Thr Gly His Leu Glu Ile Val Glu
         50                  55                  60

Val Leu Leu Lys Tyr Gly Ala Asp Val Asn Ala Trp Asp Asn Tyr Gly
 65                  70                  75                  80

Ala Thr Pro Leu His Leu Ala Ala Asp Gly His Leu Glu Ile Val
                 85                  90                  95

Glu Val Leu Leu Lys His Gly Ala Asp Val Asn Ala Lys Asp Tyr Glu
                100                 105                 110

Gly Phe Thr Pro Leu His Leu Ala Ala Tyr Asp Gly His Leu Glu Ile
```

```
                115                 120                 125
Val Glu Val Leu Leu Lys Tyr Gly Ala Asp Val Asn Ala Gln Asp Lys
        130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Asn
                165

<210> SEQ ID NO 17
<211> LENGTH: 169
<212> TYPE: PRT
<213> ORGANISM: Artificial Sequence
<220> FEATURE:
<223> OTHER INFORMATION: Synthetic 5 ANK repeat DARPin 3NOG
<220> FEATURE:
<221> NAME/KEY: PEPTIDE
<222> LOCATION: (1)..(10)
<223> OTHER INFORMATION: N-terminal His tag for purification

<400> SEQUENCE: 17

Met Arg Gly Ser His His His His His Gly Ser Asp Leu Gly Lys
  1               5                  10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Ser Asp His Val Gly Trp
        35                  40                  45

Thr Pro Leu His Leu Ala Ala Tyr Phe Gly His Leu Glu Ile Val Glu
    50                  55                  60

Val Leu Leu Lys Asn Gly Ala Asp Val Asn Ala Asp Ser Leu Gly
 65                  70                  75                  80

Val Thr Pro Leu His Leu Ala Ala Asp Arg Gly His Leu Glu Val Val
                85                  90                  95

Glu Val Leu Leu Lys Asn Gly Ala Asp Val Asn Ala Asn Asp His Asn
            100                 105                 110

Gly Phe Thr Pro Leu His Leu Ala Ala Asn Ile Gly His Leu Glu Ile
        115                 120                 125

Val Glu Val Leu Leu Lys His Gly Ala Asp Val Asn Ala Gln Asp Lys
    130                 135                 140

Phe Gly Lys Thr Ala Phe Asp Ile Ser Ile Asp Asn Gly Asn Glu Asp
145                 150                 155                 160

Leu Ala Glu Ile Leu Gln Lys Leu Asn
                165

<210> SEQ ID NO 18
<211> LENGTH: 156
<212> TYPE: PRT
<213> ORGANISM: Artificial Sequence
<220> FEATURE:
<223> OTHER INFORMATION: Synthetic Amino Acid Sequence of Wild-Type
      Human p16

<400> SEQUENCE: 18

Met Glu Pro Ala Ala Gly Ser Ser Met Glu Pro Ser Ala Asp Trp Leu
  1               5                  10                  15

Ala Thr Ala Ala Ala Arg Gly Arg Val Glu Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
```

```
                    50                  55                  60
Leu His Gly Ala Glu Pro Asn Cys Ala Asp Pro Ala Thr Leu Thr Arg
 65                  70                  75                  80

Pro Val His Asp Ala Ala Arg Glu Gly Phe Leu Asp Thr Leu Val Val
                 85                  90                  95

Leu His Arg Ala Gly Ala Arg Leu Asp Val Arg Asp Ala Trp Gly Arg
                100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
        130                 135                 140

Ile Asp Ala Ala Glu Gly Pro Ser Asp Ile Pro Asp
145                 150                 155
```

<210> SEQ ID NO 19
<211> LENGTH: 156
<212> TYPE: PRT
<213> ORGANISM: Artificial Sequence
<220> FEATURE:
<223> OTHER INFORMATION: Synthetic Amino Acid Sequence of Human p16
      Variant

<400> SEQUENCE: 19

```
Met Glu Pro Ala Ala Gly Ser Ser Met Glu Pro Ser Ala Asp Lys Leu
 1               5                  10                  15

Ala Thr Ala Ala Ala Arg Gly Arg Val Glu Val Arg Ala Leu Leu
                20                  25                  30

Glu Ala Gly Ala Asp Pro Asn Ala Pro Asn Ser Tyr Gly Arg Arg Pro
            35                  40                  45

Ile Gln Val Met Met Met Gly Ser Ala Arg Val Ala Glu Leu Leu Leu
 50                  55                  60

Lys His Gly Ala Glu Pro Asn Ser Ala Asp Pro Ala Thr Ser Thr Arg
 65                  70                  75                  80

Pro Val His Asp Ala Ala Arg Glu Gly Phe Leu Asp Thr Leu Val Val
                 85                  90                  95

Leu His Arg Ala Gly Ala Arg Leu Asp Ala Arg Asp Ala Trp Gly Arg
                100                 105                 110

Thr Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
        130                 135                 140

Ile Asp Ala Ala Glu Gly Pro Ser Asp Ile Pro Asp
145                 150                 155
```

<210> SEQ ID NO 20
<211> LENGTH: 168
<212> TYPE: PRT
<213> ORGANISM: Artificial Sequence
<220> FEATURE:
<223> OTHER INFORMATION: Synthetic mouse_p16

<400> SEQUENCE: 20

```
Met Glu Ser Ala Ala Asp Arg Leu Ala Arg Ala Ala Gln Gly Arg
 1               5                  10                  15

Val His Asp Val Arg Ala Leu Leu Glu Ala Gly Val Ser Pro Asn Ala
                20                  25                  30

Pro Asn Ser Phe Gly Arg Thr Pro Ile Gln Val Met Met Met Gly Asn
            35                  40                  45
```

```
Val His Val Ala Ala Leu Leu Asn Tyr Gly Ala Asp Ser Asn Cys
     50                  55                  60

Glu Asp Pro Thr Thr Phe Ser Arg Pro Val His Asp Ala Ala Arg Glu
 65                  70                  75                  80

Gly Phe Leu Asp Thr Leu Val Val Leu His Gly Ser Gly Ala Arg Leu
                 85                  90                  95

Asp Val Arg Asp Ala Trp Gly Arg Leu Pro Leu Asp Leu Ala Gln Glu
            100                 105                 110

Arg Gly His Gln Asp Ile Val Arg Tyr Leu Arg Ser Ala Gly Cys Ser
        115                 120                 125

Leu Cys Ser Ala Gly Trp Ser Leu Cys Thr Ala Gly Asn Val Ala Gln
    130                 135                 140

Thr Asp Gly His Ser Phe Ser Ser Ser Thr Pro Arg Ala Leu Glu Leu
145                 150                 155                 160

Arg Gly Gln Ser Gln Glu Gln Ser
                165

<210> SEQ ID NO 21
<211> LENGTH: 159
<212> TYPE: PRT
<213> ORGANISM: Artificial Sequence
<220> FEATURE:
<223> OTHER INFORMATION: Synthetic rat_p16

<400> SEQUENCE: 21

Met Glu Ser Ser Ala Asp Arg Leu Ala Arg Ala Ala Ala Leu Gly Arg
  1               5                  10                  15

Glu His Glu Val Arg Ala Leu Leu Glu Ala Gly Ala Ser Pro Asn Ala
                 20                  25                  30

Pro Asn Thr Phe Gly Arg Thr Pro Ile Gln Val Met Met Met Gly Asn
             35                  40                  45

Val Lys Val Ala Ala Leu Leu Leu Ser Tyr Gly Ala Asp Ser Asn Cys
     50                  55                  60

Glu Asp Pro Thr Thr Leu Ser Arg Pro Val His Asp Ala Ala Arg Glu
 65                  70                  75                  80

Gly Phe Leu Asp Thr Leu Val Val Leu His Gln Ala Gly Ala Arg Leu
                 85                  90                  95

Asp Val Arg Asp Ala Trp Gly Arg Leu Pro Leu Asp Leu Ala Leu Glu
            100                 105                 110

Arg Gly His His Asp Val Val Arg Tyr Leu Arg Tyr Leu Leu Ser Ser
        115                 120                 125

Ala Gly Asn Val Ser Arg Val Thr Asp Arg His Asn Phe Cys Ser Ser
    130                 135                 140

Thr Pro Arg Cys Leu Gly Leu Arg Gly Gln Pro Pro Lys Gln Arg
145                 150                 155

<210> SEQ ID NO 22
<211> LENGTH: 49
<212> TYPE: PRT
<213> ORGANISM: Artificial Sequence
<220> FEATURE:
<223> OTHER INFORMATION: Synthetic p15 protein variant
<220> FEATURE:
<221> NAME/KEY: MOD_RES
<222> LOCATION: (1)..(1)
<223> OTHER INFORMATION: Xaa is a hydrophilic amino acid, such as
      lysine, arginine, aspartic acid, glutamic acid, glutamine,
      asparagine, or serine, or leucine
<220> FEATURE:
```

```
<221> NAME/KEY: MOD_RES
<222> LOCATION: (8)..(8)
<223> OTHER INFORMATION: Xaa is a hydrophilic amino acid such as serine,
      or cysteine
<220> FEATURE:
<221> NAME/KEY: MOD_RES
<222> LOCATION: (14)..(14)
<223> OTHER INFORMATION: Xaa is a hydrophilic amino acid, such as
      serine, arginine, lysine, aspartic acid, glutamic acid,
      glutamine, or asparagine, or leucine
<220> FEATURE:
<221> NAME/KEY: MOD_RES
<222> LOCATION: (31)..(31)
<223> OTHER INFORMATION: Xaa is valine or methionine
<220> FEATURE:
<221> NAME/KEY: MOD_RES
<222> LOCATION: (35)..(35)
<223> OTHER INFORMATION: Xaa is arginine or lysine
<220> FEATURE:
<221> NAME/KEY: MOD_RES
<222> LOCATION: (42)..(42)
<223> OTHER INFORMATION: Xaa is a hydrophilic amino acid such as
      alanine, aspartic acid, glutamic acid, glutamine, or
      asparagine, or valine (V)
<220> FEATURE:
<221> NAME/KEY: MOD_RES
<222> LOCATION: (43)..(43)
<223> OTHER INFORMATION: Xaa is arginine or cysteine
<220> FEATURE:
<221> NAME/KEY: MOD_RES
<222> LOCATION: (49)..(49)
<223> OTHER INFORMATION: Xaa is a hydrophilic amino acid, such as,
      threonine, arginine, lysine, aspartic acid, glutamic acid,
      glutamine, asparagine, or serine, or leucine

<400> SEQUENCE: 22

Xaa His Gly Ala Glu Pro Asn Xaa Ala Asp Pro Ala Thr Xaa Thr Arg
  1               5                  10                  15

Pro Val His Asp Ala Ala Arg Glu Gly Phe Leu Asp Thr Leu Xaa Val
             20                  25                  30

Leu His Xaa Ala Gly Ala Arg Leu Asp Xaa Xaa Asp Ala Trp Gly Arg
         35                  40                  45

Xaa
```